United States Patent
Calabro et al.

(10) Patent No.: US 8,410,180 B2
(45) Date of Patent: Apr. 2, 2013

(54) METHODS TO TREAT URINARY INCONTINENCE

(75) Inventors: Anthony Calabro, Cleveland Heights, OH (US); Aniq B. Darr, Piscataway, NJ (US); Firouz Daneshgari, Akron, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 748 days.

(21) Appl. No.: 12/387,256

(22) Filed: Apr. 30, 2009

(65) Prior Publication Data

US 2009/0274678 A1 Nov. 5, 2009

Related U.S. Application Data

(60) Provisional application No. 61/049,275, filed on Apr. 30, 2008.

(51) Int. Cl.
*A61K 47/30* (2006.01)
(52) U.S. Cl. .................................................. 514/772.3
(58) Field of Classification Search ............... 514/772.3
See application file for complete search history.

(56) References Cited

U.S. PATENT DOCUMENTS

| | | | |
|---|---|---|---|
| 4,024,073 A | 5/1977 | Shimizu et al. |
| 4,256,596 A | 3/1981 | Cohen |
| 4,277,582 A | 7/1981 | Mueller et al. |
| 4,350,629 A | 9/1982 | Yannas et al. |
| 4,500,676 A | 2/1985 | Balazs et al. |
| 5,017,229 A | 5/1991 | Burns et al. |
| 5,128,326 A | 7/1992 | Balazs et al. |
| 5,532,221 A | 7/1996 | Huang et al. |
| 5,667,778 A | 9/1997 | Atala |
| 5,705,488 A | 1/1998 | Janzen et al. |
| 5,739,113 A | 4/1998 | Lee |
| 5,769,899 A | 6/1998 | Schwartz et al. |
| 5,783,691 A | 7/1998 | Malson et al. |
| 5,964,806 A | 10/1999 | Cook et al. |
| 5,976,526 A | 11/1999 | Atala |
| 6,060,053 A | 5/2000 | Atala |
| 6,165,489 A | 12/2000 | Berg et al. |
| 6,251,876 B1 | 6/2001 | Bellini et al. |
| 6,419,701 B1 | 7/2002 | Cook et al. |
| 6,425,854 B1 | 7/2002 | Galt et al. |
| 6,586,493 B1 | 7/2003 | Massia et al. |
| 6,982,298 B2 | 1/2006 | Calabro et al. |
| 7,060,287 B1 | 6/2006 | Hubbard et al. |
| 7,157,080 B2 | 1/2007 | Radice et al. |
| 7,368,502 B2 | 5/2008 | Calabro et al. |
| 7,465,766 B2 | 12/2008 | Calabro et al. |
| 2001/0027237 A1 | 10/2001 | Mayes et al. |
| 2004/0047892 A1 | 3/2004 | Desrosiers et al. |
| 2004/0063206 A1 | 4/2004 | Rowley et al. |
| 2004/0127698 A1 | 7/2004 | Tsai et al. |
| 2004/0185021 A1 | 9/2004 | Hubbard |
| 2005/0065616 A1 | 3/2005 | Ankorina-Stark et al. |
| 2005/0075533 A1 | 4/2005 | deVries |
| 2005/0265959 A1 * | 12/2005 | Calabro et al. ............ 424/78.27 |
| 2006/0040894 A1 | 2/2006 | Hunter et al. |
| 2006/0040895 A1 | 2/2006 | Thacker |
| 2006/0100138 A1 | 5/2006 | Olsen et al. |
| 2007/0014729 A1 | 1/2007 | Farhat et al. |
| 2009/0305983 A1 | 12/2009 | Ying et al. |
| 2010/0298628 A1 | 11/2010 | Taylor et al. |

FOREIGN PATENT DOCUMENTS

| | | |
|---|---|---|
| EP | 0 516 026 A1 | 12/1992 |
| EP | 0 718 312 A2 | 6/1996 |
| EP | 1 312 383 A2 | 5/2003 |
| JP | 54-36388 | 3/1979 |
| JP | 62-64803 A | 3/1987 |
| JP | 6-105901 A | 4/1994 |
| JP | 7-102002 | 4/1995 |
| JP | 8-85703 | 4/1996 |
| JP | 09-059303 A | 3/1997 |
| JP | 2000-041691 A | 2/2000 |

(Continued)

OTHER PUBLICATIONS

Appell, "Collagen Injection Therapy for Urinary Incontinence", Urologic Clinics of North America, vol. 21, No. 1, pp. 177-182 (Feb. 1994).*

Soffia et al., "Peroxidase-Catalyzed Crosslinking of Functionalized Polyaspartic Acid Polymers", Journal of Macromolecular Science, Part A. Pure and Applied Chemistry, vol. A39, No. 10, pp. 1151-1181 (2002).*

Office action issued Apr. 14, 2011 in U.S. Appl. No. 12/283,661.

International Search Report and Written Opinion issued Nov. 30, 2009 in corresponding PCT Application PCT/US2009/042353.

Kurisawa, M. et al., "Injectable biodegradable hydrogels composed of hyaluronic acid-tyramine conjugates for drug delivery and tissue engineering," 2005, Chem. Commun., 26, 4312-4314.

Aeschbach, R., Amado, R. and Neukom, H., "Formation of dityrosine cross-links in proteins by oxidation of tyrosine residues," Biochimica et Biophysica Acta, Protein Structure, vol. 439, No. 2, pp. 292-301, 1976.

(Continued)

*Primary Examiner* — Kevin E Weddington
(74) *Attorney, Agent, or Firm* — Pearne & Gordon LLP

(57) ABSTRACT

A method is disclosed for treatment of urinary incontinence. The method includes the steps of providing to a person or animal, in the vicinity of a pubo-urethral ligament of the person or animal, a composition including collagen macromolecules that have hydroxyphenyl side groups substituted thereon, which are reacted to form dihydroxyphenyl linkages. In an embodiment, the collagen macromolecules are gelatin macromolecules. In another embodiment, the hydroxyphenyl side groups are tyramine side groups and the dihydroxyphenyl linkages are dityramine linkages. The composition can be injected into a space between a urethra and a pubis of the person or animal wherein the pubo-urethral ligament is disposed in the space. The method is advantageous, for example, based on being minimally invasive.

32 Claims, 11 Drawing Sheets

(6 of 11 Drawing Sheet(s) Filed in Color)

FOREIGN PATENT DOCUMENTS

| | | | |
|---|---|---|---|
| JP | 2001-097908 | A | 4/2001 |
| JP | 2002-80501 | A | 3/2002 |
| JP | 2003-10308 | A | 1/2003 |
| JP | 2007-023079 | A | 2/2007 |
| WO | 85/04413 | A1 | 10/1985 |
| WO | 89/02445 | A1 | 3/1989 |
| WO | 89/07426 | A1 | 8/1989 |
| WO | 90/09769 | A1 | 9/1990 |
| WO | 93/07862 | A1 | 4/1993 |
| WO | 97/18244 | A1 | 5/1997 |
| WO | 99/57301 | A1 | 11/1999 |
| WO | 00/01733 | A1 | 1/2000 |
| WO | 00/11038 | A1 | 3/2000 |
| WO | 00/16818 | A1 | 3/2000 |
| WO | 00/37124 | A1 | 6/2000 |
| WO | 00/46252 | A1 | 8/2000 |
| WO | 00/54762 | A2 | 9/2000 |
| WO | 01/00246 | A2 | 1/2001 |
| WO | 01/00792 | A1 | 1/2001 |
| WO | 01/85845 | A1 | 11/2001 |
| WO | 02/18450 | A1 | 3/2002 |
| WO | 02/39948 | A2 | 5/2002 |
| WO | 02/060375 | A2 | 8/2002 |
| WO | 02/068383 | A2 | 9/2002 |
| WO | 03/006068 | A1 | 1/2003 |
| WO | 03/007879 | A2 | 1/2003 |
| WO | 03/018033 | A1 | 3/2003 |
| WO | 03/018044 | A1 | 3/2003 |
| WO | 03/090765 | A1 | 6/2003 |
| WO | 03/061626 | A1 | 7/2003 |
| WO | 03/072157 | A1 | 9/2003 |
| WO | 03/076475 | A1 | 9/2003 |
| WO | 2004/050712 | A1 | 6/2004 |
| WO | 2006/135843 | A2 | 12/2006 |
| WO | 2007/097710 | A1 | 8/2007 |

OTHER PUBLICATIONS

Akkara, J.A., Senecal, K.J. and Kaplan, D.L., "Synthesis and characterization of polymers produced by horseradish peroxidase in dioxane," Journal of Polymer Science, Part A: Polymer Chemistry, vol. 29, pp. 1561-1574, 1991.

Allen, R.E., Hosker, G.L., Smith, A.R.B. and Warrell, D.W., "Pelvic floor damage and childbirth: a neurophysiological study," British Journal of Obstetrics and Gynaecology, vol. 97, pp. 770-779, 1990.

Anderson, Svend Olav, "The cross-links in resilin identified as dityrosine and trityrosine," Biochimica et Biophysica Acta, General Subjects, vol. 93, No. 1, pp. 213-215, 1964.

Anderson, Svend Olav, "Regional differences in degree of resilin cross-linking in the desert locust, *Schistocerca gregaria*," Insect Biochemistry and Molecular Biology, vol. 34, pp. 459-466, 2004.

Aslam, M. and Dent, A., Bioconjugation: Protein Coupling Techniques for the Biomedical Sciences, Chapters 5 and 6, pp. 216-482, Macmillan Reference Ltd., London, 1999.

Blumenkrantz, N. and Asboe-Hansen, G., "New method for quantitative determination of uronic acids," Analytical Biochemistry, vol. 54, pp. 484-489, 1973.

Brittberg, M., Lindahl, A., Nilsson, A., Ohlsson, C., Isaksson, O. and Peterson, L., "Treatment of deep cartilage defects in the knee with autologous chondrocyte transplantation," N. Engl. J. Med., vol. 331, No. 14, pp. 889-895, 1994.

Buckwalter, J.A. and Mankin, H.J., "Articular cartilage. Part II: Degeneration and osteoarthrosis, repair, regeneration and transplantation," J. Bone Joint Surgery [Am], vol. 79A, No. 4, pp. 612-632, 1997.

Bulpitt, P. and Aeschlimann, D., "New strategy for chemical modification of hyaluronic acid: Preparation of functionalized derivatives and their use in formation of novel biocompatible hydrogels," J. Biomed. Mater. Res., vol. 47, pp. 152-169, 1999.

Calabro, A., Benavides, M., Tammi, M., Hascall, V.C. and Midura, R.J., "Microanalysis of enzyme digests of hyaluronan and chondroitin/dermatan sulfate by fluorophore-assisted carbohydrate electrophoresis (FACE)," Glycobiology, vol. 10, No. 3, pp. 273-281, 2000.

Calabro, A., Hascall, V.C. and Midura, R.J., "Adaptation of FACE methodology for microanalysis of total hyaluronan and chondroitin sulfate composition from cartilage," Glycobiology, vol. 10, No. 3, pp. 283-293, 2000.

Cannon, T.W., Sweeney, D.D., Conway, D.A., Kamo, I., Yoshimura, N., Sacks, M. and Chancellor, M.B., "A tissue-engineered suburethral sling in an animal model of stress urinary incontinence," BJU International, vol. 96, pp. 664-669, 2005.

Cannon, T.W., Wojcik, E.M., Ferguson, C.L., Saraga, S., Thomas, C. and Damaser, M.S., "Effects of vaginal distension on urethral anatomy and function," BJU International, vol. 90, pp. 403-407, 2002.

Conway, D.A., Kamo, I., Yoshimura, N., Chancellor, M.B. and Cannon, T.W., "Comparison of leak point pressure methods in an animal model of stress urinary incontinence," International Urogynecology Journal, vol. 16, pp. 359-363, 2005.

Damaser, M.S., Broxton-King, C., Ferguson, C., Kim, F.J. and Kerns, J.M., "Functional and neuroanatomical effects of vaginal distention and pudendal nerve crush in the female rat," Journal of Urology, vol. 170, pp. 1027-1031, 2003.

Darr, A. and Calabro, A., "Synthesis and characterization of tyramine-based hyaluronan hydrogels," J. Mater. Sci.: Mater. Med., vol. 20, No. 1, pp. 33-44, Jan. 2009.

De La Motte, C.A., Hascall, V.C., Calabro, A., Yen-Lieberman, B. and Strong, S.A., "Mononuclear leukocytes preferentially bind via CD44 to hyaluronan on human intestinal mucosal smooth muscle cells after virus infection or treatment with poly(I:C)," Journal of Biological Chemistry, vol. 274, No. 43, pp. 30747-30755, 1999.

Diokno, A.C., Burgio, K., Fultz, N.H., Kinchen, K.S., Obenchain, R. and Bump, R.C., "Prevalence and outcomes of continence surgery in community dwelling women," Journal of Urology, vol. 170, p. 507-511, 2003.

Gross, A.J., "The oxidation of tyramine and related compounds by peroxidase," Ph.D. Thesis, MIT, pp. 1-84, 1954.

Gross, A.J. and Sizer, I.W., "The oxidation of tyramine, tyrosine and related compounds by peroxidase," Dept. of Biology, MIT, vol. 234, No. 6, pp. 1611-1614, 1959.

Heidkamp, M.C., Leong, F.C., Brubaker, L. and Russell, B., "Pudendal denervation affects the structure and function of the striated, urethral sphincter in female rats," International Urogynecology Journal, vol. 9, pp. 88-93, 1998.

Hijaz, A., Daneshgari, F., Cannon, T. and Damaser, M., "Efficacy of a vaginal sling procedure in a rat model of stress urinary incontinence," Journal of Urology, vol. 172, pp. 2065-2068, 2004.

Hijaz, A., Daneshgari, F., Huang, X., Bena, J., Liu, G., Saffore, L. and Damaser, M., "Role of sling integrity in the restoration of leak point pressure in the rat vaginal sling model," Journal of Urology, vol. 174, pp. 771-775, 2005.

Hunziker, E.B. and Rosenberg, L.C., "Repair of partial-thickness defects in articular cartilage: Cell recruitment from the synovial membrane," J. Bone Joint Surgery [Am] vol. 78A, No. 5, pp. 721-733, 1996.

Ishii, T., "Structure and functions of feruloylated polysaccharides," Plant Science, vol. 127, pp. 111-127, 1997.

Jurvelin, J.S., Buschmann, M.D. and Hunziker, E.B., "Optical and mechanical determination of Poisson's ration of adult bovine humeral articular cartilage," J. Biomechanics, vol. 30, No. 3, pp. 235-241, 1997.

Kalra, B., Kumar, A. and Gross, R.A., "Gel formation by enzyme-selective crosslinking of tryamine decorated poly (aspartamide)," Polymer Preprints 2000, vol. 41, No. 2, pp. 1804-1805, 2000.

Kefer, J.C., Lui, G. and Daneshgari, F., "Pubo-urethral ligament transection causes stress urinary incontinence in the female rat: a novel animal model of stress urinary incontinence," Journal of Urology, vol. 179, pp. 775-778, 2008.

Kerns, J.M., Damaser, M.S., Kane, J.M., Sakamoto, K., Benson, J.T., Shott, S. and Brubaker, L., "Effects of pudendal nerve injury in the female rat," Neurourology and Urodynamics, vol. 1, pp. 53-69, 2000.

Kim, H.L., Gerber, G.S., Patel, R.V., Hollowell, C.M.P. and Bales, G.T., "Practice patterns in the treatment of female urinary incontinence: a postal and internet survey," Journal of Urology, vol. 57, pp. 45-48, 2001.

Leach, G.E., et al., "Female Stress Urinary Incontinence Clinical Guidelines Panel summary report on surgical management of female stress urinary incontinence," Journal of Urology, vol. 158, pp. 875-880, 1997.

Lin, A.S., Carrier, S., Morgan, D.M. and Lue, T.F., "Effect of simulated birth trauma on the urinary continence mechanism in the rat," Urology, vol. 52, pp. 143-151, 1998.

Lukacz, ES., Lawrence, J.M., Contreras, R., Nager, C.W. and Luber, K.M., "Parity, mode of delivery and pelvic floor disorders," Obstetrics and Gynecology, vol. 107, No. 6, pp. 1253-1260, 2006.

Malmgren, A., Uvelius, B., Andersson, K.E. and Andersson, P.O., "On the reversibility of functional bladder changes induced by infravesical outflow obstruction in the rat," Journal of Urology, vol. 143, pp. 1026-1031, 1990.

Mow, V.C., Kuei, S.C., Lai, W.M. and Armstrong, C.G., "Biphasic creep and stress relaxation of articular cartilage in compression: theory and experiments," Journal of Biomechanical Engineering, vol. 102, pp. 73-84, 1980.

Nilsson, C.G., Kuuva, N., Falconer, C., Rezapour, M. and Ulmsten, U., "Long-term results of tension-free vaginal tape (TVT) procedure for surgical treatment of female stress urinary incontinence," International Urogynecology Journal, vol. 12, Suppl. 2, pp. S5-S8, 2001.

Petros, P.E.P., "The pubourethral ligaments—an anatomical and histological study in the live patient," International Urogynecology Journal, vol. 9, pp. 154-157, 1998.

Petros, P.E.P. and Ulmsten, U.I., "An integral theory of female urinary incontinence: Experimental and clinical considerations," Acta Obstet Gynecol Scand, vol. 69, Suppl. 153, pp. 7-31, 1990.

Pouyani T., Kuo, J.W., Harbison, G.S. and Prestwich, G.D., "Solid-state NMR of N-acylureas derived from the reaction of hyaluronic acid with isotopically-labeled carbodiimides,"J. Am. Chem. Soc., vol. 114, pp. 5972-5976, 1992.

Sehgal, D. and Vijay, I.K., "A method for the high efficiency of water-soluble carbodiimide-mediated amidation," Analytic Biochemistry, vol. 218, pp. 87-91, 1994.

Sofia, S.J., Singh, A. and Kaplan, D.L., "Peroxidase-catalyzed crosslinking of functionalized polyaspartic acid polymers," Journal of Macromolecular Science, Pure and Applied Chemistry, vol. A39, No. 10, pp. 1151-1181, 2002.

Soltz, M.A. and Ateshian, G.A., "A conewise linear elasticity mixture model for the analysis of tension-compression nonlinearity in articular cartilage," Journal of Biomechanical Engineering, vol. 122, pp. 576-586, 2000.

Thorton, T.D. and Savage, P.E., "Phenol oxidation pathways in supercritical water," Ind. Eng. Chem. Res., vol. 31, No. 11, pp. 2451-2456, XP002363819, 1992.

Tomihata, K. and Ikada, Y., "Crosslinking and degradation of biopolymer," Recent Res. Devel. Biotech. & Bioeng., vol. 4, pp. 35-49, 2001.

Wells-Knect, M.C., Huggins, T.G., Dyer, D.G., Thorpe, S.R. and Baynes, J.W., "Oxidized amino acids in lens protein with age," Journal of Biological Chemistry, vol. 268, No. 17, pp. 12348-12352, 1993.

Zacharin, R.F., "The anatomic supports of the female urethra," Obstetrics and Gynecology, vol. 32, No. 6, pp. 754-759, 1968.

International Search Report and Written Opinion of the International Searching Authority for PCT Application No. PCT/US04/00478, mailed Jul. 15, 2005.

International Search Report and Written Opinion of the International Searching Authority for PCT Application No. PCT/US05/24391, mailed May 11, 2006.

Brown, A.L., Srokowski, E.M., Shu, X.Z., Prestwich, G.D. and Woodhouse, K.A., "Development of a model bladder extracellular matrix combining disulfide cross-linked hyaluronan with decellularized bladder tissue," Macromol. Biosci., vol. 6, No. 8, pp. 648-657, Aug. 2006.

Funakoshi, T., Majima, T., Iwasaki, N. Suenaga, N., Sawaguchi, N., Shimode, K., Minami, A., Harada, K. and Nishimura, S., "Application of tissue engineering techniques for rotator cuff regeneration using a chitosan-based hyaluronan hybrid fiber scaffold," Am. J. Sports Med., vol. 33, No. 8, pp. 1193-1201, 2005.

Ghosh, K., Ren, X.D., Shu, X.Z., Prestwich, G.D. and Clark, R.A.F., "Fibronectin functional domains coupled to hyaluronan stimulate adult human dermal fibroblast responses critical for wound healing," Tissue Eng., vol. 12, No. 3, pp. 601-613, 2006.

Goldberg, V.M. and Buckwalter, J.A., "Hyaluronans in the treatment of osteoarthritis of the knee: Evidence for disease-modifying activity," Osteoarthritis and Cartilage 13(3), pp. 216-224, 2005.

Handa, V.L., Jensen, J.K., Germain, M.M. and Ostergard, D.R., "Banked human fascia lata for the suburethral sling procedure: A preliminary report," Obstet Gynecol 88(6), pp. 1045-1049, Dec. 1996.

Hu, M., Sabelman, E.E., Cao, Y., Chang, J. and Hentz, V.R., "Three-dimensional hyaluronic acid grafts promote healing and reduce scar formation in skin incision wounds," J. Biomed. Mater. Res. Part B: Appl. Biomater., vol. 67, No. 1, pp. 586-592, Oct. 2003.

Lemer, M.L., Chaikin, D.C. and Blaivas, J.G., "Tissue strength analysis of autologous and cadaveric allografts for the pubovaginal sling," Neurourol Urodyn 18, pp. 497-503, 1999.

Shu, X.Z., Ahmad, S., Liu, Y. and Prestwich, G.D., "Synthesis and evaluation of injectable, in situ crosslinkable synthetic extracellular matrices for tissue engineering," J. Biomed. Mater. Res. A., vol. 79, No. 4, pp. 902-912, Dec. 2006.

Yang, S.H., Chen, P.Q., Chen, Y.F. and Lin, F.H., "An In-vitro Study on Regeneration of Human Nucleus Pulposus by Using Gelatin/Chondroitin-6-Sulfate/Hyaluronan Tri-copolymer Scaffold," Artificial Organs, vol. 29, No. 10, pp. 806-814, 2005.

Yildirim, A., Basok, E.K., Gulpinar, T., Gurbuz, C., Zemheri, E. and Tokuc, R., "Tissue reactions of 5 sling materials and tissue material detachment strength of 4 synthetic mesh materials in a rabbit model," J Urol 174, pp. 2037-2040, Nov. 2005.

Office action issued Aug. 13, 2010 in Canadian Patent Application No. 2,512,730.

English translation of Office action issued Aug. 4, 2009 in Japanese Patent Application Serial No. 2006-500869.

Extended European Search Report issued Mar. 30, 2012 in corresponding European Patent Application No. 09739831.7.

* cited by examiner

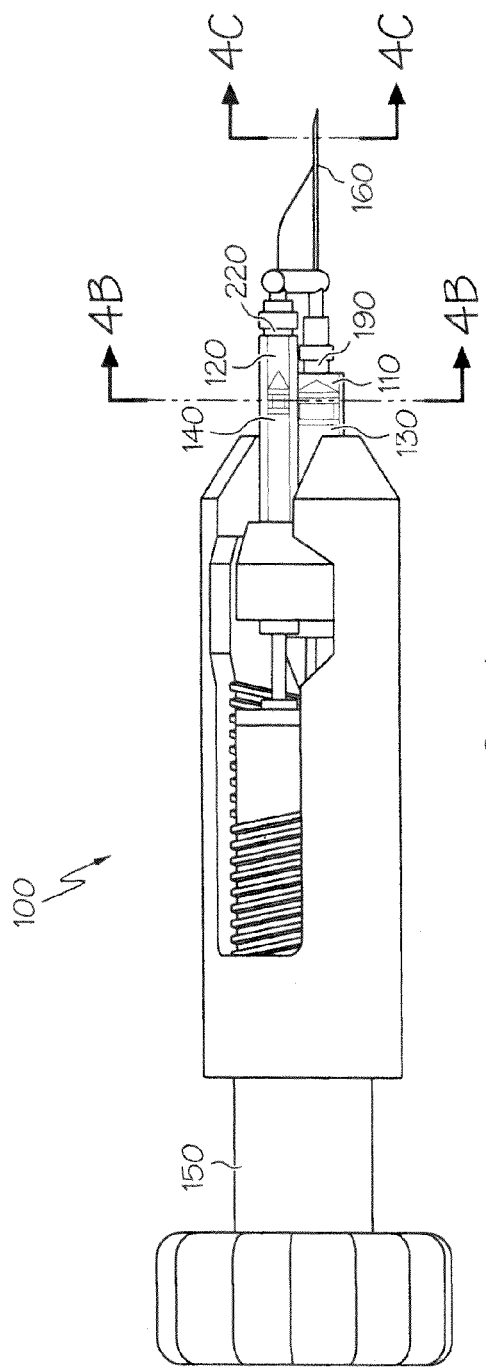
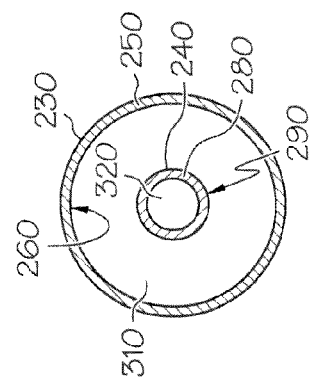
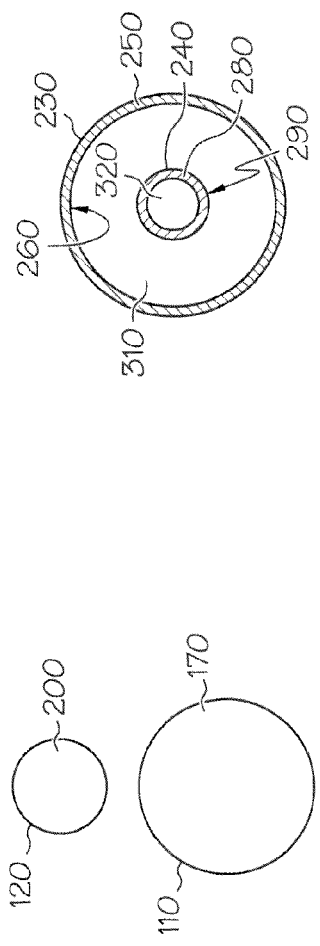
FIG. 4A
FIG. 4B
FIG. 4C

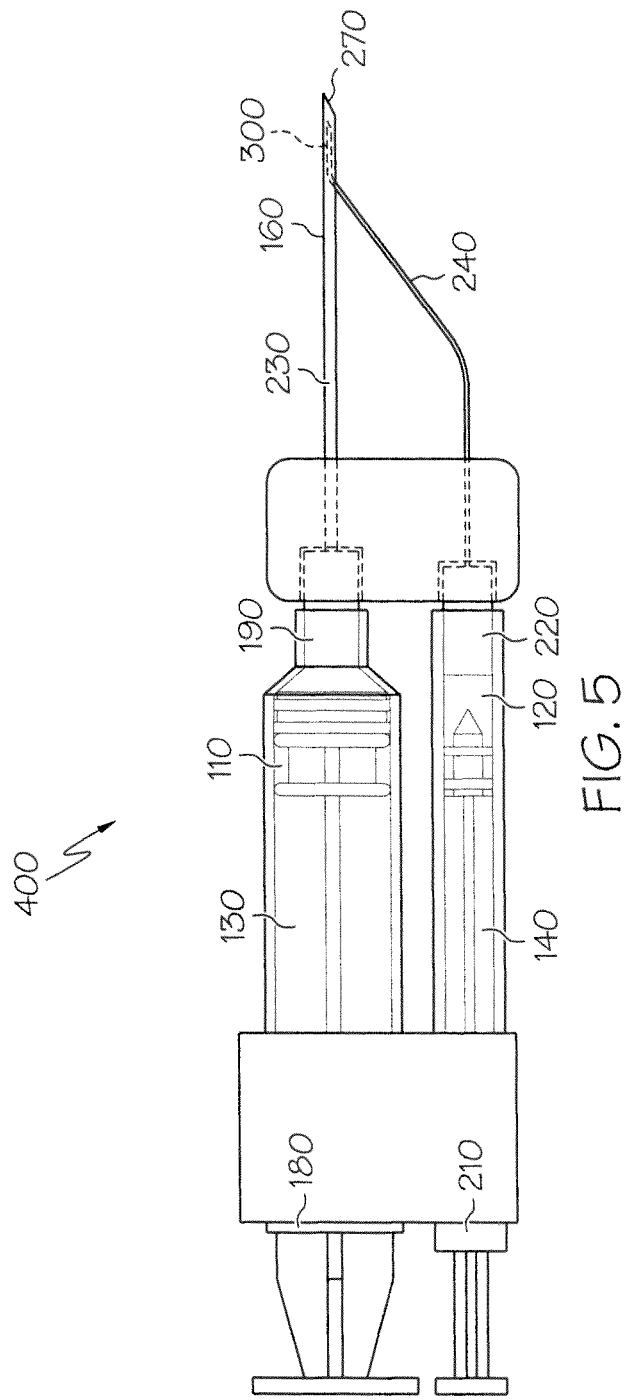

METHODS TO TREAT URINARY INCONTINENCE

CROSS-REFERENCE TO RELATED APPLICATIONS

This application claims the benefit of U.S. Provisional Application No. 61/049,275, filed Apr. 30, 2008, the entire disclosure of which is hereby incorporated herein by reference.

FIELD OF THE INVENTION

The present invention relates to methods of treatment of urinary incontinence.

BACKGROUND OF THE INVENTION

Urinary incontinence is one of the most prevalent conditions of the lower urinary tract, affecting approximately 40% of women in the United States. Stress urinary incontinence (herein abbreviated SUI) accounts for a large portion of these women. SUI is the loss of small amounts of urine associated with movements, such as coughing, sneezing, laughing, and exercise, that cause increased pressure on the bladder based on increased intra-abdominal pressure. In the US, over 160,000 surgical procedures are performed for SUI annually, and mid-urethral slings have become the most commonly performed procedure for SUI. Mid-urethral sling procedures are based on the studies of the female urethra by Petros and Ulmsten which showed that a deficient pubo-urethral ligament (herein abbreviated PUL), with attachments between the ventral surface of the urethra and the lower pubic bone (herein termed the pubis), may lead to urethral mobility and SUI or mixed urinary incontinence in women. These authors describe the role of the PUL within an "integral theory" of the pathophysiology of urinary incontinence.

In order to study the mechanisms of SUI in the female, investigators have recently developed and tested animal models in the female rat that mimic the symptoms of SUI. These investigators have used either the vaginal distension model, which causes injury to the tissues of the pelvic floor similar to birth trauma, or the model of direct injury to the pudendal or sciatic nerve, which induces manifestations of SUI. The symptoms and signs of SUI in these animal models have been assessed by in vivo measures such as leak-point pressure (herein also termed LPP), which is similar to the clinical measure of bladder outlet competency, as well as by quantitative morphometry measuring post-partum damage to the external sphincter and pudendal nerve. These models demonstrate tissue injury similar to that following birth trauma. Both the vaginal distension and the nerve injury models have been accepted as surrogates of post-partum SUI in women.

However, it is known that nulliparous women can also develop SUI. Consequently, it is believed by the present inventors that animal models of nulliparous SUI should focus on alternative anatomic targets for controlling continence during intra-abdominal stress. In 1961, Zacharin described the attachments of the PUL and the vaginal insertion of the anterior portion of the levator ani, and was the first to suggest the role of these structures in continence. In 1998, Petros analyzed the structure and insertions of the PUL in female patients during the intra-vaginal slingplasty procedure. Petros described the PUL as descending like a fan from the pubis and including a urethral part, a vaginal part, and thin fibrous threads connecting the two parts, which appears as a continuous sheet of connective tissue. Petros further described that the urethral and vaginal parts each generally vary between 5-7 mm in width and 3-4 mm in thickness, with the urethral part being about 2 cm long and inserting into the midpart of the urethra, and the vaginal part being about 3-4 cm long and inserting into the vaginal hammock posterolaterally, about 1 cm short of the bladder neck. The insertion of the urethral part into the midpart of the urethra (also termed urethral attachment), has been hypothesized to provide ventral tethering of the urethra during intra-abdominal strain, preventing urethral mobility and subsequent leak.

Based on the postulated role of PUL in SUI, recent surgical treatments for SUI based on the "integral theory" have led to the development of mid-urethral slings, pioneered by the transvaginal tape sling procedure. This procedure, introduced by Ulmsten and Petros, has enjoyed worldwide popularity with excellent long term efficacy. It is estimated that over one million sling procedures have been performed worldwide. However, the sling procedure is not without morbidity, and a more simplified procedure with the potential to reduce morbidity and pain for the patient would be desirable.

BRIEF SUMMARY OF THE INVENTION

The following presents a simplified summary of the invention in order to provide a basic understanding of some example aspects. This summary is not an extensive overview of the invention. Moreover, this summary is not intended to identify critical elements of the invention nor delineate the scope of the invention.

In accordance with one aspect, a method of treating urinary incontinence is provided. The method includes the steps of providing to a person or animal, in a vicinity of a pubo-urethral ligament of the person or animal, a composition including collagen macromolecules that have hydroxyphenyl side groups substituted thereon, wherein at least a portion of the hydroxyphenyl side groups are reacted to form dihydroxyphenyl linkages.

In accordance with another aspect, another method of treating urinary incontinence is provided. The method includes the steps of injecting a composition into a space between a urethra and a pubis of a person or animal wherein a pubo-urethral ligament is disposed in the space. The composition includes collagen macromolecules that have tyramine side groups substituted thereon. The tyramine side groups are reacted to form dityramine linkages.

In accordance with another aspect, another method of treating urinary incontinence is provided. The method includes injecting a first precursor into a space between a urethra and a pubis of a person or animal wherein a pubo-urethral ligament is disposed in the space. The first precursor includes gelatin macromolecules that have tyramine side groups substituted thereon, and a peroxidase or a peroxide but not both. In the first precursor, the ratio of the tyramine side groups to the sum of the tyramine side groups and all amino acids in the gelatin macromolecules is about or less than 5%. A second precursor is also injected into the aforementioned space. The second precursor includes the other of the peroxide and peroxidase not included in the first precursor. The tyramine side groups on the gelatin macromolecules from the first precursor are reacted with peroxide in the presence of peroxidase, at least one of the latter being from the second precursor, to form dityramine linkages.

In accordance with another aspect, a kit is provided. The kit includes collagen macromolecules that have hydroxyphenyl side groups substituted thereon, a first container, and a second container. The first container includes a peroxidase or a peroxide. The second container includes the other of the peroxidase and peroxide that is not included in the first container. The first and/or second container(s) optionally include(s) at least a portion of the collagen macromolecules that have hydroxyphenyl side groups substituted thereon.

BRIEF DESCRIPTION OF THE DRAWINGS

The file of this patent contains at least one drawing executed in color. Copies of this patent with color drawings will be provided by the Patent Office upon request and payment of the necessary fee.

FIG. 4A shows an example of a dual syringe injection device including a screw device activator.

FIG. 4B shows an enlarged view of a cross-section of the first and second barrels of the dual syringe injection device along line 4B of FIG. 4A.

FIG. 4C shows an enlarged view of a cross-section of the first and second needles of the dual syringe injection device along line 4C of FIG. 4A.

FIG. 5 shows an example of a dual syringe injection device lacking a screw device activator.

DESCRIPTION OF EXAMPLE EMBODIMENTS

Figure 1:
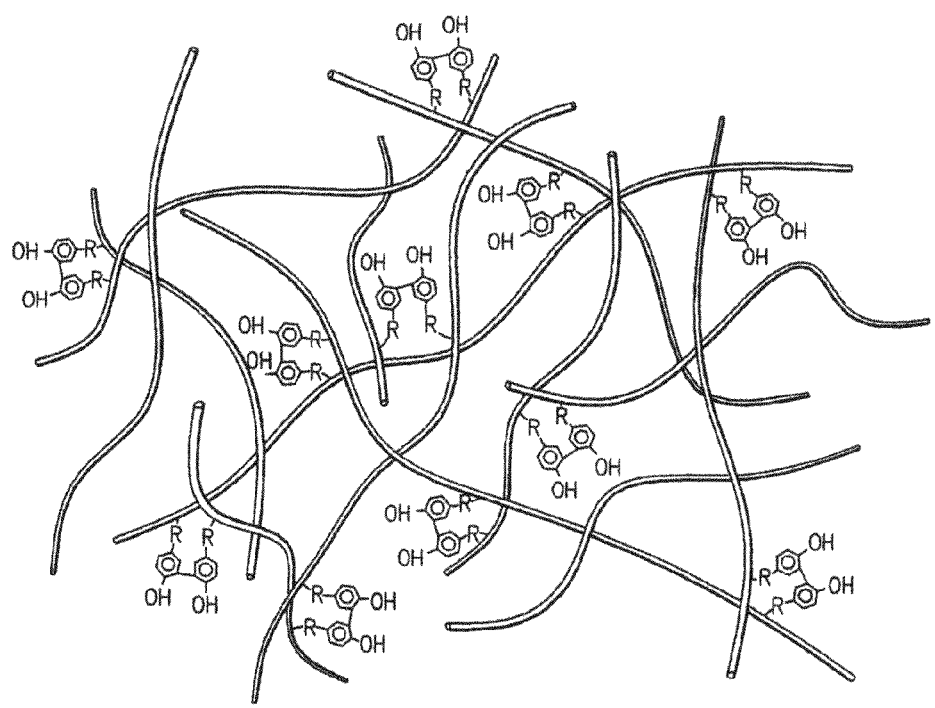
FIG. 1 shows a schematic illustration of a dihydroxyphenyl cross-linked macromolecular network.

Example embodiments are described below and illustrated in the drawings. These embodiments are not intended to be limitations. For example, one or more aspects can be utilized in other embodiments and even other devices or methods.

As indicated above, it has been believed that SUI can be caused by a deficient PUL, and more specifically by the failure of the deficient PUL to prevent urethral mobility upon application of intra-abdominal pressure. Without wishing to be bound by theory, it is now believed that contacting a deficient PUL of a person or animal having SUI with a composition including collagen macromolecules that have hydroxyphenyl side groups substituted thereon, and thereafter reacting the hydroxyphenyl groups to form dihydroxyphenyl linkages, promotes scarring and strengthening of the PUL, resulting in effective treatment of SUI (e.g. greater than 80% or 90% reduction in occurrences of SUI in the person or animal). Alternatively, the hydroxyphenyl groups can be reacted to form the dihydroxyphenyl linkages contemporaneously or in conjunction with the provision of the aforementioned composition in contact with or in the vicinity of the deficient PUL. For example, the dual-syringe device described below can be used to provide two solutions in the vicinity of the PUL, such that cross-linking to form dihydroxyphenyl linkages is initiated at the same time as, or in conjunction with, providing the composition in that vicinity. It is believed that upon reacting the collagen macromolecules having hydroxyphenyl side groups substituted thereon form a plurality of intermolecular cross-links (via dihydroxyphenyl linkages), wherein a resulting collagen macromolecular network, or network of cross-linked collagen macromolecules, promotes scarring of the deficient PUL, which in turn results in strengthening of the PUL. Moreover it is believed that the cross-linked collagen macromolecules cannot readily diffuse away from the PUL, in contrast for example to collagen macromolecules that are not cross-linked, and that this contributes to the scarring and strengthening of the PUL. Further still, it is believed that the cross-linked collagen macromolecules will ultimately be degraded by proteases that normally occur in the body, resulting in a scarred and strengthened PUL that is substantially free of the cross-linked collagen macromolecules.

As also indicated above, it has been believed that animal models of nulliparous SUI should focus on alternative anatomic targets for controlling continence during intra-abdominal stress. Without wishing to be bound by theory, it is now believed that transection of the PUL of a rat provides a useful model of nulliparous SUI in the rat based on the PUL playing a role in tethering the urethra to the pubis and preventing urethral mobility and subsequent leak.

As used herein, the term collagen refers to a long, fibrous structural protein that is a major component of the extracellular matrix, which provides support to tissues and structure to cells. Collagen includes naturally occurring ("natural") collagens, such as type I, type II, type III, and type IV collagens, and engineered collagens, such as collagens available from FibroGen, Inc. (San Francisco, Calif.) and other commercial sources. Collagen also includes collagen in forms of any type, including single-stranded and multi-stranded collagenous proteins or polypeptides, the tropocollagen helix comprised of three polypeptide strands, such as type I collagen, and denatured-collagen products that substantially retain their native or engineered primary amino acid sequence. Such denatured-collagen products can be produced, for example, through hydrolysis or partial hydrolysis of the native or engineered fibrous collagen proteins, and include gelatin. Accordingly, it will be appreciated that modified or truncated collagenous proteins, such as gelatin, fall within the scope of collagen as used herein, as do more fibrous proteins, such as full length collagens.

Collagen can be derived from any of various naturally-occurring sources, including humans and animals, and can be isolated and prepared according to conventional methods. Collagen can also be prepared or engineered synthetically based on amino acid and nucleic acid sequences for any of the various collagen types using conventional methods of molecular biology and protein expression. Likewise, gelatin can be produced from native or engineered collagens, or from denatured collagenous proteins, through conventional hydrolysis or other techniques as known in the art.

As used herein, the term hydroxyphenyl side group refers to a substituent of, for example, a macromolecule, such as a collagen macromolecule, wherein the substituent includes a hydroxyphenyl group. A suitable hydroxyphenyl side group is a tyramine side group. A plurality of collagen macromolecules that include a plurality of hydroxyphenyl side groups can be used to form a collagen macromolecular network, also termed a collagen hydrogel. Both a collagen macromolecule that includes a hydroxyphenyl side group substituted thereon and a collagen macromolecular network can be prepared by applying to collagen various methods disclosed in U.S. Pat. Nos. 6,982,298, 7,368,502, and 7,465,766, the contents of all of which are incorporated herein by reference in their entirety.

In brief, in accordance with the incorporated patents, a cross-linked macromolecular network, as shown schematically in FIG. 1, can be prepared in two steps, the first step being covalent coupling of a plurality of molecules of a hydroxyphenyl compound to a plurality of macromolecules to yield a plurality of macromolecules including hydroxyphenyl side groups, and the second step being cross-linking of a plurality of the hydroxyphenyl side groups to yield the cross-linked macromolecular network. More specifically, in the first step, hydroxyphenyl groups are covalently-coupled to the macromolecules, periodically or randomly along their length, via a carbodiimide-mediated reaction. In one embodiment, the covalent coupling can be accomplished between polycarboxylate macromolecules, or macromolecules that include carboxyl groups (or the cognate carboxylate groups, depending on pH), and molecules of a hydroxyphenyl compound that include a primary amine group. In another embodiment, the covalent coupling can be accomplished between polyamine macromolecules, or macromolecules including primary amine groups, and molecules of a hydroxyphenyl compound that includes a carboxyl group (or, again, the cognate carboxylate group, depending on pH). In either embodiment, the carbodiimide-mediated reaction catalyzes covalent coupling of the macromolecules and the molecules of the hydroxyphenyl compound through the carboxyl groups and primary amine groups. In the second step, the hydroxyphenyl-substituted macromolecules are cross-linked via a dihydroxyphenyl linking structure that is formed between hydroxyphenyl side groups on different macromolecules. Of note, some dihydroxyphenyl linking may also occur between different hydroxyphenyl side groups attached to the same macromolecule. In one embodiment, peroxidase in the presence of a dilute peroxide is able to extract the phenolic hydroxyl hydrogen atom from a hydroxyphenyl containing compound or side group, such as a tyramine side group, leaving the phenolic hydroxyl oxygen with a single unshared electron, an extremely reactive free radical. The free radical isomerizes to one of the two equivalent ortho-position carbons and then two such structures dimerize to form a covalent bond effectively cross-linking the structures, which after enolizing generates a dihydroxyphenyl dimer, e.g. a dihydroxyphenyl linkage such as a dityramine linkage. A suitable peroxide includes hydrogen peroxide ($H_2O_2$). A suitable peroxidase is horseradish peroxidase (herein abbreviated HRP). Alternatively, any other suitable enzyme or other agent can be used that is capable of generating free-radicals for cross-linking macromolecules that contain hydroxyphenyl side groups. Considering the peroxidase enzyme in more detail, the peroxidase can either form hydroxyphenyl radicals required for cross-linking through interaction of hydroxyphenyl groups at the enzyme active site to directly create the desired radicals, or through generation of superoxide radicals, which then diffuse from the enzyme and interact with hydroxyphenyl groups to generate the desired radicals. Other compounds that have the potential to produce the same effect include any porphyrin containing compound, which includes the peroxidase family, hemoproteins, or the structurally related chlorin compounds. A number of other free radical initiators can also be used to crosslink the hydroxyphenyl-modified long-chain macromolecules, as described in detail in the patents incorporated above.

The methods disclosed in the patents incorporated above can be applied to collagen, to yield first a collagen macromolecule with a hydroxyphenyl group substituted thereon and second a collagen macromolecular network, as follows. Collagen macromolecules include a plurality of carboxyl groups, which can be covalently linked to hydroxyphenyl compounds that include a primary amine group via the carbodiimide-mediated reaction. Hydroxyphenyl compounds that are suitable for the reaction include tyramine (also termed 4-(2-Aminoethyl)phenol; 4-hydroxyphenethylamine; tyrosamine; 2-p-hydroxyphenylethylamine; p-β-aminoethylphenol; or α-(4-hydroxyphenyl)-β-aminoethane) and tyrosine (also termed L-Tyrosine; Tyr; Y; β-(p-hydroxyphenyl)alanine; α-amino-p-hydroxyhydrocinnamic acid; (S)-α-amino-4-hydroxybenzenepropanoic acid). Of note, collagen macromolecules also include a plurality of primary amine groups, which may be covalently linked to hydroxyphenyl compounds that include a carboxyl group, also via the carbodiimide-mediated reaction. However, in collagen, the mole percent of amino acids with amine side chains is much lower than the mole percent of amino acids with carboxyl side chains. Also of note, covalent coupling of carboxyl groups and primary amine groups of the same and different collagen macromolecules may also occur. Such covalent coupling, to the extent that it may occur under the methods described below, does not appear to interfere with efficacy.

Figure 2:
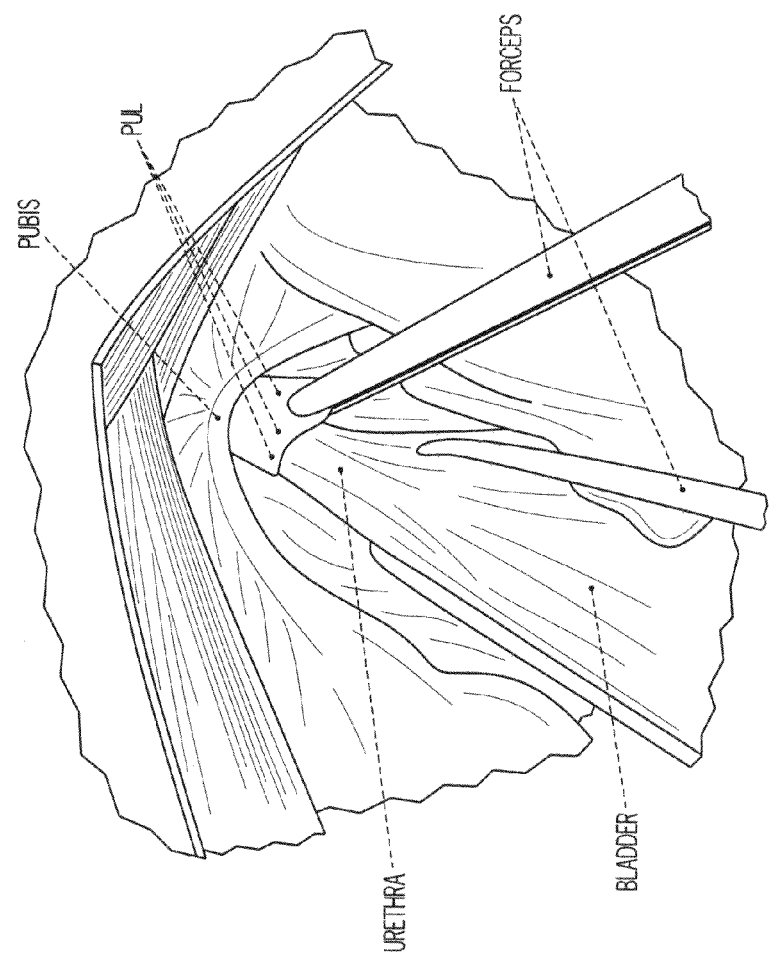
FIG. 2 shows a drawing of a PUL space of a rat.
Figure 3:
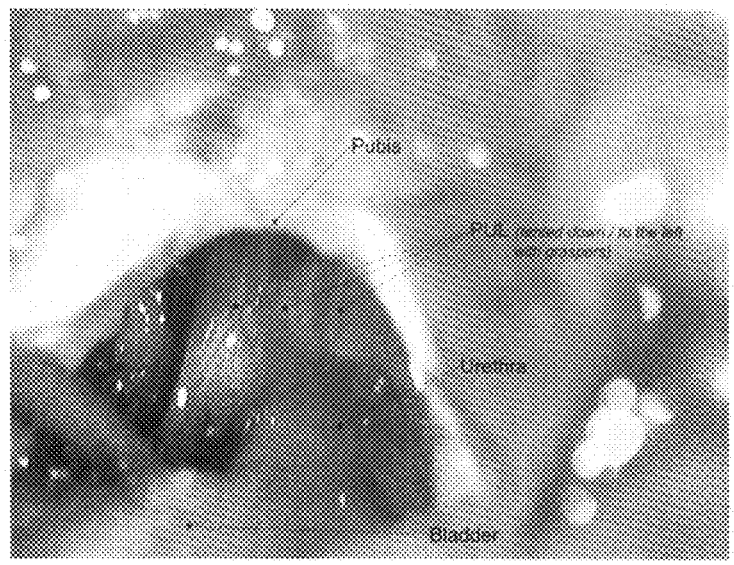
FIG. 3 shows a photograph of a PUL space of a rat.

As indicated above, a method of treatment of stress urinary incontinence is provided. The method can include a step of providing to a person or animal, in a vicinity of a pubo-urethral ligament of the person or animal, a composition comprising collagen macromolecules that have hydroxyphenyl side groups substituted thereon. The vicinity of the pubo-urethral ligament includes, for example, a space between a urethra and a pubis of the person or animal, the space comprising the pubo-urethral ligament and herein also termed the PUL space. The vicinity of the pubo-urethral ligament also includes fascia underlying and supporting the urethra. The anatomy of the PUL space in particular in a rat is shown in an illustration and a photograph in FIGS. 2 & 3, respectively. As indicated above, the PUL has been described as descending like a fan from the pubis and including a urethral part that is inserted into the midpart of the urethra. As also indicated above, the insertion of the urethral part into the midpart of the urethra, or the urethral attachment, has been hypothesized to provide ventral tethering of the urethra during intra-abdominal strain, preventing urethral mobility and subsequent leak.

Suitable collagen macromolecules include, for example, type I collagen, type II collagen, type III collagen, type IV collagen, other native collagens, synthetic or engineered forms or types of collagen, highly purified recombinant collagen, collagen that is a component of a tissue extract, such as gelatin, and collagen that is a product of denaturation and hydrolysis of a naturally occurring, synthetic, or engineered collagen that substantially retains its primary amino-acid sequence, again such as gelatin. Regarding type I collagen in particular, suitable ranges of average molecular weight include, for example, 60,000-120,000 Daltons.

More particularly, suitable collagen macromolecules include gelatin macromolecules. As indicated above, gelatin is a partially hydrolyzed form of collagen. More specifically, gelatin is a heterogeneous mixture of water-soluble proteins of high average molecular weights, present in collagen, the proteins having been extracted from any one of various types of animals by boiling skin, tendon, ligaments, bones, and other organs in water. Gelatin is commercially available in various types, including type A, which is acid-cured gelatin, and type B, which is lime-cured gelatin. Gelatin can be produced from various animals, including pig (i.e. porcine gelatin), cow (i.e. bovine gelatin), and fish (i.e. gelatin from the skin of cold-water fish). Gelatin can be produced in various ranges of average molecular weights, including 20,000-25,000, 40,000-50,000, and 50,000-100,000 Daltons. A suitable gelatin can include any of the various gelatins commercially available from Sigma-Aldrich Inc. (St. Louis, Mo.).

Suitable hydroxyphenyl side groups include, for example, tyramine side groups and suitable dihydroxyphenyl linkages include, for example, dityramine linkages. As indicated above, by applying the methods of the above-incorporated patents to collagen, molecules of tyramine can be covalently coupled with collagen macromolecules, specifically based on reaction of the primary amines of the molecules of tyramine and the carboxyl groups of the collagen macromolecules, to yield collagen macromolecules that have tyramine side groups substituted thereon. Suitable hydroxyphenyl groups may also include tyrosine side groups and other side groups that are structurally similar to tyramine or tyrosine side groups.

The collagen macromolecules can have a degree of tyramine substitution such that the molar ratio of the tyramine side groups to the sum of the tyramine side groups and all amino acids in the collagen macromolecules is about or less than 5%. The tyramine substitution occurs at available sites on the collagen macromolecules, specifically at free carboxyl groups of glutamic acid residues, aspartic acid residues, and carboxyl-terminal residues of the collagen macromolecules. More particularly, the collagen macromolecules can have a degree of tyramine substitution so that the aforementioned ratio is about 1% to about 5%, about 1.5% to about 4%, or about 2% to about 3%. The degree of tyramine substitution (the foregoing ratio) can be determined, for example, based on preparing tyramine-substituted collagen macromolecules, conducting amino acid analysis based on acid hydrolysis, separating the tyramine and individual amino acids based on high performance liquid chromatography, and quantifying the tyramine and the sum of the tyramine and the individual amino acids. Without wishing to be bound by theory, it is believed that use of collagen macromolecules having a suitable degree of tyramine substitution provides an advantage in terms of intermolecular cross-linking that is sufficiently high for formation of a collagen macromolecular network but sufficiently low to allow most of the cross-linked collagen macromolecules to substantially maintain a native conformation, structural integrity, and effectiveness.

The providing step can include a step of introducing the composition into the PUL space. The introducing step can be accomplished, for example, by injection, applying, spraying, brushing, wiping, pouring, or other appropriate medical, surgical, or experimental means. For example, injection into the space may be accomplished by positioning the needle of a syringe in the space and injecting the composition including the collagen macromolecules that have hydroxyphenyl side groups substituted thereon into the space. This approach would provide an advantage in terms of being minimally invasive, in contrast to a more highly invasive surgery such as is required for the conventional sling procedure. Alternatively, applying, spraying, brushing, wiping, or pouring could be used where the space had become accessible, for example based on a surgical incision. The terms providing and introducing can also be used interchangeably with the term administering. A suitable composition includes collagen macromolecules that have hydroxyphenyl side groups substituted thereon and that are dissolved, suspended, or otherwise provided in a liquid phase, to promote ease of introduction into the space.

As indicated above, the collagen macromolecules that have hydroxyphenyl side groups substituted thereon can be injected into the PUL space of the person or animal, where the pubo-urethral ligament is located. Alternatively or additionally, an injection could be made not directly into the PUL space but otherwise in the vicinity of the PUL, to provide additional amounts of the collagen macromolecules that have hydroxyphenyl side groups substituted thereon that, for example, may flow toward the PUL, prevent diffusion of other injected matter away from the PUL, and/or, upon being cross-linked, provide additional support to tissue in the vicinity of the PUL, for example the fascia underlying and supporting the urethra to which the PUL is attached. This approach also would provide an advantage in terms of being minimally invasive. Again, a suitable composition includes collagen macromolecules that have hydroxyphenyl side groups substituted thereon and that are dissolved, suspended, or otherwise provided in a liquid phase, to promote ease of injection into the person or animal.

In accordance with another aspect, the injecting step comprises using a first needle and a second needle, the second needle being partially located inside the first needle, for example concentrically. The first needle and second needle are described in more detail below. The use of the first needle and the second needle would provide an advantage in terms of promoting rapid and sufficient mixing of the collagen macromolecules that have hydroxyphenyl side groups substituted thereon, a catalyst, and an activator, to promote uniformity of cross-linking of the hydroxyphenyl side groups upon injection into a person or animal, as described in more detail below.

The method can also include a step of reacting the hydroxyphenyl side groups of substituted collagen macromolecules to form dihydroxyphenyl linkages subsequent to injecting or otherwise providing in vivo the substituted collagen macromolecules. For example, by applying to collagen molecules that have hydroxyphenyl side groups substituted thereon the methods of the above-incorporated patents, the tyramine side groups can be cross-linked to form dityramine linkages and a corresponding collagen macromolecular network, wherein a plurality of dityramine linkages constitute intermolecular cross-links. Without wishing to be bound by theory, it is believed that covalent coupling of a collagen macromolecule and tyramine, which includes a primary amine group but lacks a carboxyl group, provides an advantage relative to covalent coupling of a collagen macromolecule and a compound including both a primary amine group and a carboxyl group, by providing greater control over the extent and sites of covalent modification of the collagen macromolecule.

The linkages can be formed by treating the hydroxyphenyl side groups with a peroxidase and a peroxide. As indicated above, the methods of the above-incorporated patents can be applied to form a collagen macromolecular network based on cross-linking, as catalyzed by a peroxidase and activated by a peroxide. Suitable peroxidases include horseradish peroxidase and other biocompatible peroxidases. Suitable peroxides include hydrogen peroxide and other biocompatible peroxides. As used herein, biocompatible means capable of use without impermissibly detrimental effect on living tissues. Treating the hydroxyphenyl side groups with a peroxidase and a peroxide once the hydroxyphenyl-substituted collagen macromolecules are provided in the PUL space provides a new biomaterial including a collagen macromolecular network coating or integrated into the PUL or other surrounding tissue. The use of a peroxidase and a peroxide provide the advantage of allowing the cross-linking to occur in situ, for example following a minimally invasive injection, because peroxidase is a naturally occurring biomolecule and peroxide, when used as a dilute solution, will not harm the body. In situ cross-linking also provides the advantage of allowing the collagen macromolecular network to form as a coating based on the precise shape of the PUL, given that the collagen macromolecules that have hydroxyphenyl side groups substituted thereon would coat the PUL prior to and/or during cross-linking and that the corresponding collagen macromolecular network would then form in a manner complementary to the shape of the PUL.

To achieve in situ cross-linking, the collagen composition, upon injection, can further include a peroxidase or a peroxide but not both, the other of the peroxidase or the peroxide being injected in a separate composition. For example, a first composition can include the collagen macromolecules that have hydroxyphenyl side groups substituted thereon and the peroxidase, and a second composition can include the peroxide. Alternatively, the first composition can include the collagen macromolecules that have hydroxyphenyl side groups substituted thereon and the peroxide, and the second composition can include the peroxidase. In either case, the second composition can also include collagen macromolecules that have hydroxyphenyl side groups substituted thereon. The first and second compositions can be prepared and stored in advance of being provided to the person or animal. The first and second compositions can be provided or injected and mixed simultaneously, for example by use of the first needle, the second needle, and a syringe, as described in detail below. Alternatively, the first and second compositions can be provided sequentially and mixed in situ. The combination of the collagen macromolecules and the peroxidase or peroxide in a single composition in advance of providing or injecting the composition into the PUL space provides the advantage of allowing uniform mixing in advance.

The reacting step, wherein the hydroxyphenyl (e.g. tyramine) side groups on the collagen macromolecules react to generate cross-links results in strengthening of the pubourethral ligament. Without wishing to be bound by theory, it is believed that formation of the collagen macromolecular network in situ in contact with the PUL will provide increased support for the PUL in the short term before scarring can occur (e.g. by serving as a glue), compensating for a deficiency of the PUL, restoring proper ventral tethering of the urethra during intra-abdominal strain, and preventing urethral mobility and subsequent leak before scarring is achieved. It is also believed that this will promote healing of the deficiency of the PUL, wherein scarring of the PUL yields a remodeled PUL having a restored capability to support the urethra and raise its leak point pressure. It is further believed that the collagen macromolecular network will ultimately be degraded by naturally occurring proteases, with continued proper ventral tethering of the urethra by the PUL being sustained by a remodeled PUL through scarring. Formation of the collagen macromolecular network in situ in contact with the PUL will provide advantages by promoting healing of the PUL and by avoiding reliance on long-term stability and function of a foreign material introduced into the body.

The method can further include a step of testing for stress-induced urination by the person or animal. Regarding a person, the testing can be based on increasing intra-abdominal pressure, for example by having the person cough or laugh or by applying physical pressure, and observing whether urination occurs. In an animal, the testing can be based on leak point pressure, as described in detail below.

As indicated above, a kit is also provided. The kit can include collagen macromolecules that have hydroxyphenyl side groups substituted thereon, a first container, and a second container. The first container can include a peroxidase or a peroxide. The second container can include the other of the peroxidase and peroxide that is not included in the first container. The first and/or second container(s) can optionally include at least a portion of the collagen macromolecules that have hydroxyphenyl side groups substituted thereon.

The kit can also include instructions for the use of the kit in the treatment of urinary incontinence. The instructions can specify, for example, that the contents of the first container can be administered to a person or animal contemporaneously or in conjunction with the contents of the second container. The instructions can also specify that the type of urinary incontinence to be treated is, for example, stress urinary incontinence.

The various aspects described above can be practiced individually or in combination with one or more of the other aspects.

Preliminary experiments have been carried out in rats to test the effectiveness of the above-disclosed methods for treatment of SUI, particularly regarding use of dityramine-cross-linked gelatin. The dityramine-cross-linked gelatin is made in accordance with the above-disclosed methods based on covalently coupling of molecules of tyramine with gelatin macromolecules to yield gelatin macromolecules that have tyramine side groups substituted thereon, followed by cross-linking the tyramine side groups to form dityramine linkages to produce the dityramine-cross-linked gelatin. Gelatin macromolecules can be initially substituted with tyramine residues at an appropriate degree of substitution. Regarding cross-linking, a first composition can be prepared that includes the gelatin macromolecules in combination with peroxidase enzyme, both at appropriate concentrations in an appropriate solution or buffer. A second composition can also be prepared that contains the same or a different concentration of gelatin macromolecules that have tyramine side groups substituted thereon in combination with dilute hydrogen peroxide. The first and second compositions can then be injected at the same time or near in time to one another within the PUL space. Upon combination and mixing of the two compositions, the cross-linking reaction initiates, causing formation of dityramine cross-links and resulting in formation of dityramine-cross-linked gelatin, a hydrogel, in situ within the PUL space. Without wishing to be bound by theory, it is believed that by becoming cross-linked in situ, the dityramine cross-linked gelatin is able to penetrate surrounding tissues, including the PUL, and become intimately incorporated therein, to form a more robust support structure. Such a dityramine cross-linked gelatin, formed in situ in the PUL space, has been suggested in experiments to restore the leak point pressure to normal or near normal in rats whose PULs were previously transected to simulate SUI, with corresponding reductions in leak-point pressure, as described in more detail below.

The appropriate concentrations of gelatin macromolecules (or more generally, collagen macromolecules), peroxidase enzyme, and hydrogen peroxide to be used in the first composition and the second composition can be calculated based on appropriate ranges of final concentrations to be obtained upon mixing of the first composition and second composition. Appropriate ranges of final concentrations can be, for example, as follows: gelatin macromolecules (or more generally, collagen macromolecules) (50-100 mg/ml); peroxidase enzyme (7.5-12.5 units/ml); and hydrogen peroxide (0.03%-0.3%). Accordingly, where the first composition and the second composition are prepared as 2× concentrated solutions, both including gelatin macromolecules, the first composition can include peroxidase enzyme at 15-25 units/ml, the second composition can include hydrogen peroxide at 0.06-0.6%, and both the first and second compositions can include gelatin macromolecules at 50-100 mg/ml.

Injection can be carried out, for example, as follows. Collagen macromolecules having tyramine side groups substituted thereon are initially prepared and suspended in a suitable carrier, such as sterile saline or other biocompatible buffer. A peroxidase enzyme, such as horseradish peroxidase, is then added to the carrier. The resulting mixture is provided in a first syringe. A second syringe is also prepared, preferably containing the same preparation of collagen macromolecules having tyramine side groups substituted thereon and the same carrier or a compatible carrier. Dilute hydrogen peroxide is then added to the carrier in the second syringe. The materials from the two syringes can then be injected into the PUL space transcutaneously in a minimally-invasive office procedure. Optionally, needle positioning can be guided by radiographic or ultrasonic means as known in the art. The injection provides an advantage given that it can be performed as a minimally invasive procedure, based merely on use of a needle puncture to deliver the relevant precursors for in situ set-up, rather than, for example, conventional therapies to treat urinary incontinence, such as sling procedures, which require more highly invasive surgery.

While cross-linking of collagen macromolecules, such as gelatin macromolecules, can be achieved via dityramine linkages, other dihydroxyphenyl linkages also may be used, e.g. via carbodiimide-mediated substitution and linking of suitable hydroxyphenyl side groups on the collagen or other polycarboxylate macromolecules. Other suitable hydroxyphenyl side groups include various hydroxyphenyl side groups that are disclosed in the above-incorporated patents. Moreover, other suitable modes to catalyze formation of the dihydroxyphenyl linkages, besides the peroxidase/peroxide pathway, may also be used, as also disclosed in the above-incorporated patents. The other suitable modes include modes for which cross-linking in situ within the PUL space can be carried out. Furthermore, direct incorporation of cells and biologics into the macromolecular networks to induce healing is also contemplated, as described in the above-incorporated patents.

As indicated above, injection of precursors of a dihydroxyphenyl-cross-linked hydrogel can be carried out by use of a first needle and a second needle, the second needle being partially located inside the first needle. Such an injection is advantageous in terms of providing mixing of the precursors during the course of injection, specifically as the precursors emerge from the needles into the site of injection, and thereby promoting the initiation of formation of the dihydroxyphenyl-cross-linked hydrogel in situ immediately upon injection. In this manner, it will be appreciated that reaction to form the dihydroxyphenyl linkages is carried out contemporaneously or in conjunction with providing the composition that will form the hydrogel within the PUL space in the vicinity of (preferably in contact with) the PUL.

The injection can be carried out, for example, by use of a dual-syringe injection device 100 that includes a first barrel 110, a second barrel 120, a first plunger 130, a second plunger 140, a single actuator 150, and a needle-inside-a-needle device 160, such as the device shown in FIG. 4A. As shown in FIGS. 4B & 5, the first barrel 110 has an internal radial area 170, a plunger port 180, and a port 190 for attachment of the needle-inside-a-needle device 160. The second barrel 120 also has an internal radial area 200, a plunger port 210, and a port 220 for attachment of the needle-within-a-needle device 160. The internal radial area 170 of the first barrel 110 is greater than the internal radial area 200 of the second barrel 120 by a defined factor (e.g. a factor of twenty). As shown in FIGS. 4A & 5, the first plunger 130 can be inserted into the plunger port 180 of the first barrel 110. Likewise, the second plunger 140 can be inserted into the plunger port 210 of the second barrel 120. The single actuator 150 can be screw-driven. As shown in FIGS. 4C and 5, the needle-inside-a-needle device 160 can include a first needle 230 and a second needle 240. The first needle 230 has a wall 250, with an inner surface 260, and an exit port 270, and is provided in fluid communication with the first barrel 110 when attached via the port 190 to the needle-inside-a-needle device 160. The second needle 240 has a wall 280, with an outer surface 290, and an exit port 300 that is located just inside or adjacent the exit port 270 for the first needle 230. The second needle 240 is provided in fluid communication with the second barrel 120 when attached via the port 220 to the needle-inside-a-needle device 160. The barrels 110 and 120 can be connected to the needle-inside-a-needle device 160 via conventional luer-lock fittings, wherein a female such fitting can be provided or machined in the device 160 capable to receive the male fittings on the barrels that define the ports 190 and 220. The first needle 230 and second needle 240 exhibit a concentric-needle arrangement, such that part of the second needle 240 is located inside part of the first needle 230. The first needle 230 has an internal radial area 310. Likewise, the second needle 240 has an internal radial area 320. The internal radial area 310 of the first needle 230 corresponds particularly to an annular area between the outer surface 290 of the wall 280 of the second needle 240 and the inner surface 260 of the wall 250 of the first needle 230. The internal radial area 310 of the first needle 230 can be greater than the internal radial area 320 of the second needle 240 by the same defined factor as between the internal radial areas of the corresponding barrels 110 and 120 (e.g. a factor of twenty).

Returning to FIG. 4A, the dual syringe injection device 100 can be operated as follows. The single actuator 150 can be used to drive the first plunger 130 and the second plunger 140 simultaneously and at the same longitudinal rate through the first barrel 110 and the second barrel 120, respectively, resulting in a volumetrically proportional extrusion of a first solution from the first barrel 110 and a second solution from the second barrel 120, wherein the volumetric rate of injection of the first solution is related to that of the second solution by the defined factor mentioned above. As shown in FIG. 5, during extrusion the first solution passes from the first barrel 110, through the port 190 and into the needle-inside-a-needle device 160, into the first needle 230, and through the exit port 270 of the first needle 230. Likewise, the second solution passes from the second barrel 120, through the port 220 and into the needle-inside-a-needle device 160, into the second needle 240, and through the exit port 300 of the second needle 240. As will be appreciated, the first and second solutions will first come into contact just inside or at the terminus of the first needle 230, where the two ports 270 and 300 are adjacently disposed. Turning to FIG. 4C, the relationship between the internal radial area 310 of the first needle 230 and the internal radial area 320 of the second needle 240 maintains the same longitudinal flow rate of the first solution and the second solution through the first needle 230 and the second needle 240, respectively, again resulting in a volumetrically proportional extrusion of the first and second solutions.

Alternatively, a dual syringe injection device 400 can omit the actuator 150 but can otherwise be identical or similar to the dual syringe device 100, as shown in FIG. 5. The device 400 can be operated by simultaneously depressing the first plunger 130 and second plunger 140.

Also alternatively, as will be evident from FIGS. 4B & 4C, the relative dimensions of the first barrel 110 and the second barrel 120 and the first needle 230 and the second needle 240 may be varied to obtain different relative barrel and/or needle diameters and correspondingly different flow-path radial areas for the first and second solutions. For example, the first barrel 110 and the second barrel 120 can be designed such that the internal radial area 170 of the first barrel 110 and the internal radial area 200 of the second barrel 120 are identical. This would produce identical volumetric flow rates of the two solution extrusions. Otherwise, the factor between the aforementioned first and second barrel radial areas can be selected to achieve the desired stoichiometric ratio between the solutions extruded from each one; for example to achieve a desired stoichiometry for a reaction between reactants contained in the two respective solutions. Alternatively or in addition, the first needle 230 and the second needle 240 can be designed such that the internal radial area 310 of the first needle 230 and the internal radial area 320 of the second needle 240 are identical. This could produce identical velocities of the two solution extrusions.

Various aspects of the device design can be easily modified to accommodate the requirements of specific clinical applications. For example, barrel or needle length, diameter, composition, etc. can be modified to allow for direct injection to a tissue during open surgery or through more minimally invasive techniques such as transcutaneous or percutaneous injection directly into a tissue or after first traversing a sinus or vessel to gain tissue access. The needles may be modified in terms of shape of their exit ports (i.e. beveled, blunt, etc.) and their relative orientations (i.e. even, askew, etc.). The barrels can also be selected to have the same or different interior diameters depending on the clinical application; likewise the needle bores (i.e. the respective bores of the two concentric needles in the vicinity of the exit port) can be selected to have different proportions than described above, so long as the interior needle will fit within the bore of the exterior needle and leave a sufficient annulus to permit the passage of fluid.

In accordance with this example and the various modifications described therein, injection results in a cylinder shaped extrusion of the first and second solutions such that the two solutions are juxtaposed against each other, with the first solution forming a ring around the second solution as viewed in cross-section. The entire assembly of the dual syringe injection device is designed to tolerate high pressures generated during actuation due to the viscous nature of the first solution. The entire assembly is easily sterilized. Preferably the barrels and plungers are disposable, transparent, and adaptable to use in standard centrifuges.

A method is also disclosed for modeling stress urinary incontinence in rats, including the steps of transecting a pubourethral ligament of a rat and testing for incontinence in the rat. The method can simulate SUI, for example nulliparous SUI, in rats. The observed clinical efficacy of mid-urethral slings, which is based on the concept of PUL deficiency in human, prompted investigation into the effects of PUL deficiency in a small animal model. The PUL in the female rat is similar in structure, insertion, and origin to that described by Petros in the human female. This structure could easily be identified in the animal and thus transected sharply without damage to other peri-urethral structures. The role of PUL deficiency in altering leak point pressures in the female rat was investigated. A rat model for SUI based on PUL deficiency was created. The model was validated through comparison with an established animal model of SUI produced via pudendal nerve transection, as described in EXAMPLE 1, below.

The method can include a step of anaesthetizing a rat. The anesthetizing step can include injection of an anesthetic composition into the rat. For example, an anesthetic can be injected intramuscularly. Other conventional means of injection of an anesthetic may also be used. The anesthetic composition can include, for example, a mixture of ketamine hydrochloride and xylazine. Other anesthetic compositions can include other conventional anesthetics, in addition to or in place of ketamine hydrochloride and/or xylazine. The method can also include a step of exposing the PUL based on a surgical incision. The surgical incision can be based on taking an anterior abdominal approach to expose the PUL through a 2 cm long incision in the lower abdomen. The method can also include a step of inserting a tube into the bladder of the rat. The bladder may be isolated for insertion of the tube, for example, based on making a 2 cm incision through the abdominal wall of the rat. The step of testing for incontinence in the rat can include a step of measuring leak point pressure in the rat. The testing step can include a step of anesthetizing the rat. The testing step can also include a step of providing intravesical pressure. The step of providing intravesical pressure can be based on pushing down and slightly caudally on the lower abdomen of the rat to increase pressure on the bladder of the rat.

The protocol for the new rat model for PUL-deficiency-induced SUI, including methods to validate the model to simulate SUI, is as follows. Leak point pressure is used as a measure of stress urinary incontinence, as previously described in Hijaz, A. et al., Efficacy of a vaginal sling procedure in a rat model of stress urinary incontinence, J. Urol., 172: 2065, 2004, the contents of which are incorporated herein by reference. The animal is anaesthetized with an intramuscular injection of a mixture of 100 mg/kg of ketamine hydrochloride (KETASET; Fort Dodge Laboratories, Fort Dodge, Iowa) and 10 mg/kg of xylazine (ROMPUN; Miles, Shawnee Mission, Kans.). The abdomen is shaved and prepped with an iodine scrub solution and alcohol. An anterior abdominal approach is taken to expose the PUL through a 2 cm long incision in the lower abdomen. The PUL is exposed atraumatically with bilateral access to the ligament. The PUL is sharply incised in the PUL transection group, and the sham group has the PUL intact. A 2 cm incision is made using aseptic technique through the abdominal wall, and using gentle dissection, the bladder is isolated. A suprapubic tube is inserted into the bladder. The dissection is continued caudally to the pelvis, and the rat pubo-urethral ligament (PUL) is isolated. After careful identification and dissection the PUL, the PUL is transected to disrupt the PUL. The incision is then closed using 3-0 VICRYL brand absorbable, synthetic, braided sutures, in a two layer closure with suture knots buried under the skin to minimize skin discomfort to the rat. Ketoprofen 5 mg/kg is used daily for pain control during the post-op period. During the anesthesia recovery phase, the rats are monitored hourly until they are alert and able to take in food and water. After a 48 hour healing period, during which the rats are assessed for infection and discomfort two times per day, the leak point pressures are measured. The rats are again fully anaesthetized with ketamine and xylazine at the above doses. Following anesthesia, intravesical pressure is provided by a Credé maneuver. A Credé maneuver is performed by placing one or two fingers gently on the abdomen of the anaesthetized rat, and gently pushing down and slightly caudally on the lower abdomen to increase pressure on the bladder. Pressure is applied at a constant rate as monitored through the suprapubic tube until leakage is noted. Leak point pressure is defined as the minimum intravesical pressure needed to cause leakage. One group of rats undergoes PUL transection as described above. An identical control group of rats undergoes sham surgery without PUL disruption. All procedures and measurements are done at the same experimental setting. In each animal leak point pressure is measured 5 times before and after surgery and the mean from each measurement is taken. Pair wise differences in leak point pressure between the true and sham PUL transections are calculated using the Wilcoxon signed rank test with p<0.05 considered significantly different. The PUL has been described by many authors as playing a role in SUI. The protocol is also described in the publication, Kefer J C, Liu G, Daneshgari F, Pubo-Urethral Ligament Transection Causes Stress Urinary Incontinence in the Female Rat: A Novel Animal Model of Stress Urinary Incontinence, *J. Urol.*, Vol. 179, No. 2, pp. 775-778, February 2008 (pub'd online Dec. 14, 2007), which is incorporated herein by reference.

Further aspects of the invention will be understood in conjunction with one or more of the following examples, which are provided by way of illustration and not limitation.

EXAMPLE 1

This example describes validation of the method for modeling SUI in rats, as disclosed above. The method was carried out according to the protocol described above. Briefly, a total of 21 female age matched Sprague-Dawley rats (Harlan, Indianapolis, Ind.) were randomly assigned to 5 groups. Groups 1 and 2 corresponded to PUL transection and sham PUL transection, respectively, with leak point pressure measured post-operatively at day 4. Groups 3 and 4 corresponded to the same treatments, respectively, except that leak point pressures were measured post-operatively at day 10. Group 5 corresponded to bilateral pudendal nerve transection, with leak point pressures measured postoperatively at day 4. PUL transection entailed leaving the surrounding tissue as well as the connection points of the PUL to both the urethra and the pelvic bone intact. The sham PUL transection involved similar surgical procedures as for the PUL transection treatment except that the PUL was not transected. Leak point pressure was measured in all groups via a suprapubic catheter. The Wilcoxon signed rank test was used to evaluate differences between the groups.

Results were as follows. Four days after surgery leak point pressure was significantly decreased in the PUL transection group 1 compared to that in the sham PUL transection group 2 after 4 days (mean±SEM 16.3 cm±2.74 vs 36.6±8.39 cm $H_2O$, p<0.00001), although it was no different from that in the pudendal nerve transection group 5 (14.5±1.06 cm H2O, p<0.44). Ten days after surgery leak point pressure remained significantly lower in the PUL transection group 3 compared to that in the sham treated group 4 (17.6±6.36 vs 31.2±5.14 cm H2O, p<0.00001), indicating the durability of PUL transection for inducing stress urinary incontinence in female rats. Furthermore, subsequent experiments have shown that unlike the traditional models for SUI, namely the vaginal-distension or pudendal nerve-crush models reported in the literature, the PUL transection model described herein did not result in spontaneous recovery of treated animals.

The results indicate that the protocol disclosed above produces a good model for SUI, wherein the leak-point pressure in rats who have undergone transection of the PUL exhibit reduced leak point pressures that are characteristic of SUI. A more detailed discussion of the experimental results is contained in the above-incorporated article by Kefer et al.

EXAMPLE 2

This example illustrates an embodiment wherein gelatin having tyramine side groups substituted thereon (herein also termed TS-gelatin) was cross-linked and used to reverse the effects of SUI simulated via the PUL transection model described above.

A total of 6 female age-matched Sprague-Dawley rats (Harlan, Indianapolis, Ind.) weighing 220 to 280 grams were randomly assigned to either of two groups. Group 1 corresponded to transection of the PUL followed by injection of TS-gelatin, peroxidase, and peroxide (n=4). Group 2 corresponded to transection of the PUL without subsequent injection of TS-gelatin, peroxidase, or peroxide (n=2). Leak point pressure was measured 6 weeks post-operatively. For both groups, LPP was determined in each anaesthetized animal via a previously implanted suprapubic catheter. Details of surgical and urodynamic procedures are provided in detail below. Briefly, PUL transection was carried out according to the method indicated above. Group 1 animals were further treated by introduction of TS-gelatin. The gelatin corresponded to porcine gelatin (Sigma, St. Louis, Mo.). The gelatin macromolecules were substituted with tyramine to provide a molar ratio of tyramine groups to total tyramine groups plus amino-acid residues of about 2.2% as described above.

Pubo-Urethral Ligament Transection (PULT) and Injection: The rats were prepared for aseptic surgery. From a midline suprapubic incision, the midurethra was identified. Reverse trendelenburg positioning was used to adequately visualize the retropubic space. The pubo-urethral ligament was identified (see FIGS. 2 & 3) and sharply incised. For the rats injected with TS-gelatin, two solutions of a 70 mg/ml TS-gelatin, designated Solution A and Solution B, were used. Solution A also included 20 units/ml of horseradish peroxidase. Solution B also included 0.6% hydrogen peroxide. The Sigma porcine gelatin used had a bloom strength of about 300, corresponding to a molecular weight in the range of 50,000-100,000 Daltons. A dual syringe injection device (Fibrijet, Micromedics Surgical Products, Saint Paul, Minn.) was used to inject the hydrogel precursor components, with one syringe filled with Solution A and the other syringe filled with Solution B. The injection device enabled simultaneous injection from both syringes, each through its own needle running substantially parallel and adjacent to the other, once the terminal ends of the two needles were positioned to deliver the hydrogel components in the PUL space. Approximately 0.2 ml total of TS-gelatin (0.1 ml from each of Solutions A and B) was injected between the urethra and pubis, corresponding to the PUL space. The solutions exiting the adjacent needle bores mixed in the PUL space to initiate cross-linking. Incisions were closed in layers with 5-zero VICRYL brand sutures for the abdominal muscle and 4-zero VICRYL brand sutures for the skin.

Suprapubic Tube Implantation: Suprapubic tube insertion was performed as modified from the method of Malmgren et al., On the reversibility of functional bladder changes induced by infravesical outflow obstruction in the rat, J. of Urol., 143: 1026, 1990, which is incorporated herein by reference. Briefly, rats were anaesthetized by a single intraperitoneal injection of ketamine hydrochloride 100 mg/kg (KETASET; Fort Dodge Laboratories, Fort Dodge, Iowa) and of xylazine 10 mg/kg (ROMPUN; Miles, Shawnee Mission, Kans.). A purse-string suture with 6-zero chromic was placed on the bladder dome. A 1 mm incision was made in the bladder in the center of the purse string suture, through which PE-50 tubing with a flared tip was inserted in the bladder, and the purse-string suture was secured around the tube. The tube was then tunneled through the abdominal wall and subcutaneous tissue to the nape of the neck and secured into place with 5-zero VICRYL sutures (Ethicon) until LPP testing.

Leak Point Pressure Testing: The LPP testing was performed as described by Damaser et al., Functional and neuroanatomical effects of vaginal distention and pudendal nerve crush in the female rat, J. Urol., 170: 1027, 2003, which is incorporated herein by reference. Two days after implantation of the suprapubic tube and while under anesthesia with urethane (1.2 g/kg; intraperitoneal injection), the rats were placed supine at the level of zero pressure and the bladder emptied manually. Subsequently, the bladder was filled with saline at room temperature (1 ml per minute) through the suprapubic catheter, while bladder pressure was recorded. The suprapubic catheter was connected to a syringe pump (Kent Scientific Corp., Torrington, Conn.) and a pressure transducer (Grass Instrument Division, Astro-med, Inc., West Warwick, R.I.). All bladder pressures were referenced to air pressure at the level of the bladder. Pressure and force transducer signals were amplified (Grass Instrument Division, Astro-med, Inc.) and digitalized for computer data collection using PolyView software (BioBench, version 1.2, National Instruments Corp., Austin, Tex.) at 10 samples per second. Peak bladder pressure was calculated for each LPP measurement at half-bladder capacity by slowly and manually increasing abdominal pressure until a leak occurred, and external pressure was immediately withdrawn. LPP measurements were performed nine times per rat. The bladder was emptied using the Credé maneuver, as described above, and refilled between LPP measurements.

Figure 6:
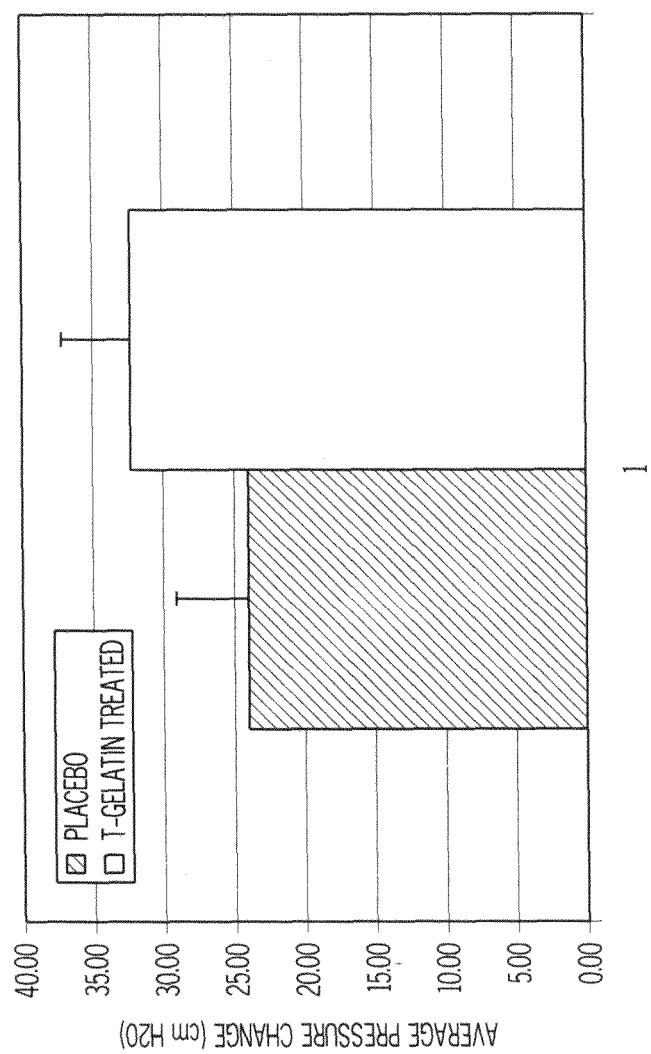
FIG. 6 shows the results for leak point pressure analyses of rats subjected to PUL transection with or without subsequent formation of a dityramine cross-linked gelatin macromolecular network in the PUL space.
Figure 7A:
FIGS. 7A-7H show the results of histological analyses of tissue of PUL spaces of rats treated as follows: (A,B,D) PUL transection; (C) PUL transection+saline; (E,F) PUL transection+cross-linked TS-gelatin; and (G,H) PUL transection+cross-linked HMW TS-HA; as tested at the following time points: (A,C,E,G) 6 weeks; and (B,D,F,H) 3 months.
Figure 7B:
Figure 7C:
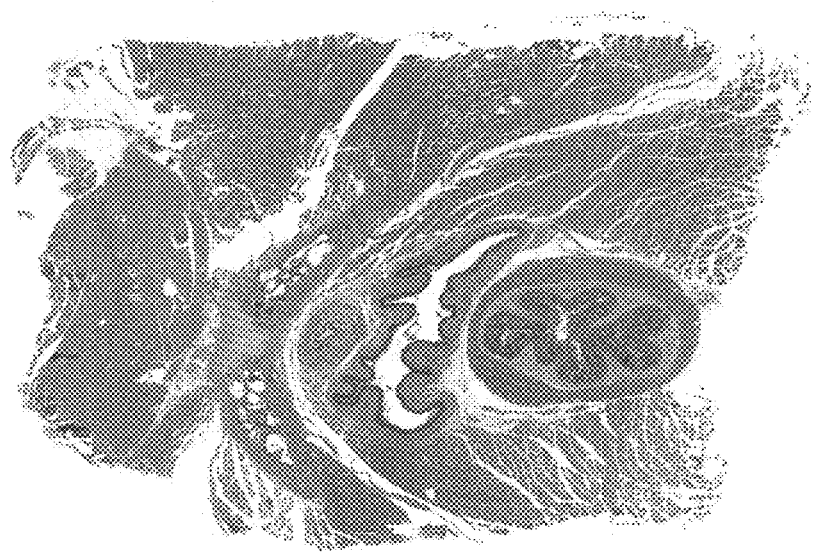
Figure 7D:
Figure 7E:
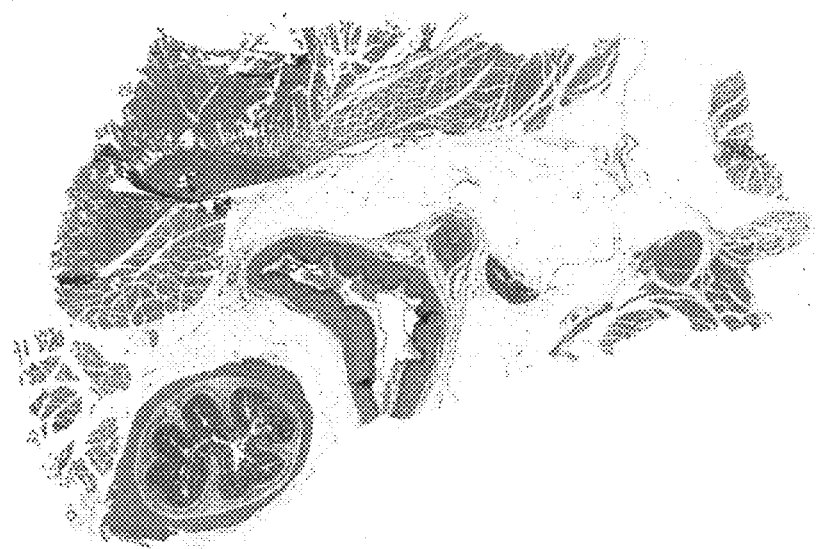
Figure 7F:
Figure 7G:
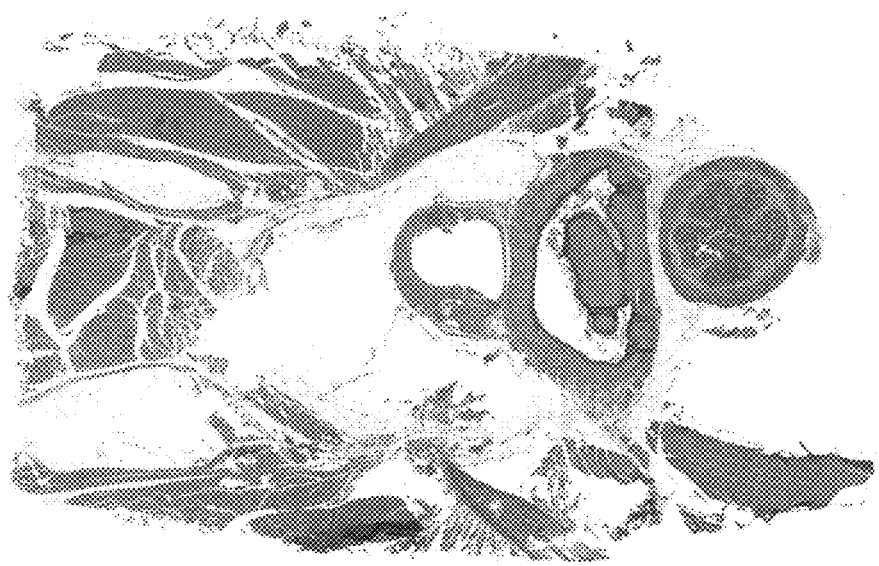
Figure 7H:

The results of this experiment are shown in FIG. 6. The LPP for the untreated group remains low as result of transection of the PUL while the LPP values for the hydrogel treated group have recovered to normal LPP values (30-40 cm of $H_2O$).

EXAMPLE 3

This example illustrates comparison of the effectiveness of various collagen macromolecules having tyramine side groups substituted thereon, specifically gelatin and human type-I collagen fragment, relative to various nonimmunogenic macromolecules having tyramine side groups substituted thereon, specifically high molecular weight hyaluronic acid and low molecular weight hyaluronic acid, in reversing the effects of PUL transection in the SUI model in rats.

The experiments were carried out as described in EXAMPLE 2 above, with the following differences. Rats were distributed among 11 groups. Group 1 corresponded to untreated rats (i.e. no-treatment, negative control). Group 2 corresponded to sham PUL transection (i.e. no PUL transection, negative control). Group 3 corresponded to PUL transection. Group 4 corresponded to PUL transection followed by injection of saline. Group 5 corresponded to PUL transection followed by injection of peroxidase and peroxide. Group 6 corresponded to PUL transection followed by injection of gelatin (i.e. non-substituted, non-cross-linked gelatin). Group 7 corresponded to PUL transection followed by injection of TS-gelatin (i.e. non-cross-linked TS-gelatin). Group 8 corresponded to PUL transection followed by injection of TS-gelatin, peroxidase, and peroxide (i.e. cross-linked TS-gelatin). Group 9 corresponded to PUL transection followed by injection of high molecular weight (~910 kDa) hyaluronic acid having tyramine side groups substituted thereon, peroxidase, and peroxide (i.e. cross-linked HMW TS-HA). Group 10 corresponded to PUL transection followed by injection of low molecular weight (~132 kDa) hyaluronic acid having tyramine side groups substituted thereon, peroxidase and peroxide (i.e. cross-linked LMW TS-HA). Group 11 corresponded to PUL transection followed by injection of human type-I collagen fragment having tyramine side groups substituted thereon, peroxidase, and peroxide (i.e. cross-linked TS-human type-I collagen). Sample sizes are indicated in the table, below. HMW TS-HA, LMW TS-HA, and TS-human-type-I-collagen were prepared by a method analogous to that disclosed above for preparation of TS-collagen. HMW TS-HA and LMW TS-HA were each substituted with tyramine at approximately 5% of available sites. Human type-I collagen fragment was substituted with tyramine similarly to gelatin. The human type I collagen fragment used corresponded to rhGelatin 100 Kd, a product of Fibrogen (San Francisco, Calif.). This recombinant protein fragment is produced by cloning and expressing defined segments of the human alpha1 (I) procollagen gene that encodes for the alpha1 (I) helical domain of human type I collagen. This product (Lot Number 06AE001HR) comprised 80.4% total protein by weight, of which ≧99% was the type I collagen fragment having a molecular weight of 100 to 110 kDa. It was initially supplied in solid powder form, and after tyramine-substitution was dissolved in sterile saline for in vitro delivery and cross-linking. The concentrations of HMW TS-HA and LMW TS-HA were ~5 and ~35 mg/ml, respectively. The concentrations were chosen to match as closely as possible the rheological properties of all materials before and after cross-linking. LPP values were determined based on at least four urinary events per rat per time point, as shown in TABLE 1.

TABLE 1

LPP results for rats of various treatment groups, as tested at time points of six weeks and three months.

| Group | Description | Average pressure difference (cm water) | Standard deviation | N |
|---|---|---|---|---|
| Six week time point |||||
| 1 | Untreated | 38.86 | 9.84 | 5 |
| 2 | Sham PULT | 32.42 | 3.33 | 4 |
| 3 | PULT | 34.24 | 10.99 | 7 |
| 4 | PULT + saline | 34.55 | 14.19 | 4 |
| 5 | PULT + P/P | 35.37 | 11.22 | 4 |
| 6 | PULT + gelatin | 30.55 | 12.36 | 6 |
| 7 | PULT + TS-gelatin | 24.99 | 6.46 | 5 |
| 8 | PULT + TS-gelatin + P/P | 35.18 | 10.06 | 7 |
| 9 | PULT + HMW-HA + P/P | 34.52 | 9.94 | 7 |
| 10 | PULT + LMW-HA + P/P | 38.86 | 11.51 | 6 |
| 11 | PULT + type-I-collagen + P/P | 42.33 | 22.74 | 8 |
| Three month time point |||||
| 1 | Untreated | 29.15 | 4.08 | 3 |
| 2 | Sham PULT | 29.25 | 4.10 | 3 |
| 3 | PULT | 43.39 | 13.43 | 6 |
| 4 | PULT + saline | 36.70 | 4.30 | 4 |
| 5 | PULT + P/P | 31.51 | 8.74 | 4 |
| 6 | PULT + gelatin | 41.50 | 17.54 | 7 |
| 7 | PULT + TS-gelatin | 38.60 | 7.10 | 7 |
| 8 | PULT + TS-gelatin + P/P | 34.48 | 6.28 | 5 |
| 9 | PULT + HMW-HA + P/P | 34.69 | 8.09 | 8 |
| 10 | PULT + LMW-HA + P/P | 36.20 | 8.33 | 6 |
| 11 | PULT + type-I-collagen + P/P | 44.48 | 23.06 | 8 |

The data represent the differences between leak and resting pressures and are expressed as averages for each group at each time point, with standard deviations and sample sizes also indicated. The following abbreviations are used in the Table: n = sample size; PULT = PUL transection; P/P = peroxidase and peroxide; TS = tyramine substituted; HMW = high molecular weight; LMW = low molecular weight; type-I-collagen = human type-I collagen fragment.

Figure 8:
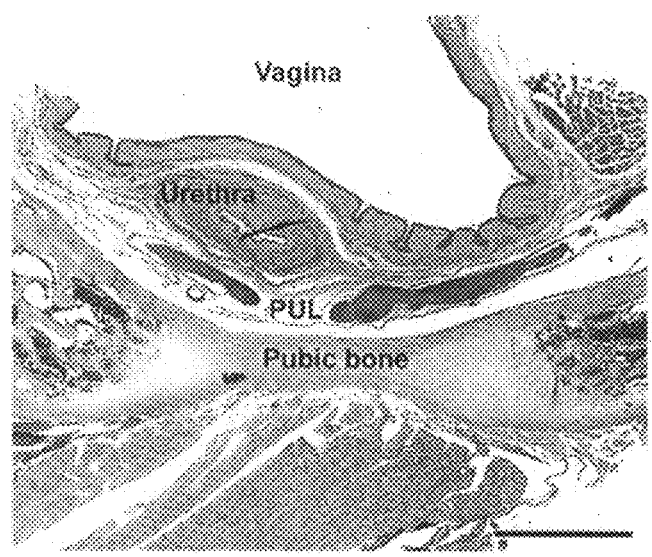
FIG. 8 shows the results of histological analysis of tissue of the PUL space of a rat subjected to sham PUL transection.

Histological analyses were also conducted regarding tissue derived from the PUL spaces of the rats of various treatment groups, at time points of six weeks and three months, according to a standard protocol based on use of hematoxylin and eosin stain. The results are shown in FIGS. 7A-7H & 8. FIGS. 7A-7H correspond to the following: (A,B,D) PUL transection; (C) PUL transection+saline; (E,F) PUL transection+cross-linked TS-gelatin; and (G,H) PUL transection+cross-linked HMW TS-HA. Time points for the analyses were as follows: (A,C,E,G) 6 weeks; and (B,D,F,H) 3 months. FIG. 8 corresponds to sham PUL transection.

As indicated above, the LPP data were inconclusive. Contrary to expectations, the treatment corresponding to PULT transection followed by injection of TS-collagen, peroxidase, and peroxide did not exhibit a higher average LPP than the various negative controls, such as the treatments corresponding to untreated, sham PUL transection, PUL transection, and PUL transection followed by injection of saline. It is believed that the unexpected results for the negative controls were due to small sample size and variation in size of the space created by PUL transection and thus the injected volume required.

The qualitative review of results of the histological analyses by an independent pathologist suggest adhesive effects on treated cases in comparison to saline injection. Further quantitative assessment of these results would require additional experiments.

The disclosed methods have been performed in a PUL-transection model for SUI. However, that is not to be construed as to exclude application of the method to other forms of urinary incontinence, e.g. mixed urinary incontinence or other causes of urinary incontinence, e.g. nerve damage, or certain patient populations, e.g. men, nulliparous women, or child bearing women. The disclosed methods may be useful to treat other forms of urinary incontinence as well, besides SUI, in animals, including humans and other mammals. Moreover, while the PUL-transection model described above has been disclosed in rats, it is contemplated that a similar model could be produced in higher animals and other mammals as well.

Although the above-described embodiments constitute the preferred embodiments, it will understood that various changes or modifications can be made thereto without departing from the spirit and scope of the present invention as set forth in the appended claims.

What is claimed is:

1. A method of treating urinary incontinence comprising providing to a person or animal, in a space between a urethra and a pubis of the person or animal wherein the person's or animal's pubo-urethral ligament is disposed in the space, a composition comprising collagen macromolecules that have hydroxyphenyl side groups substituted thereon, at least a portion of said hydroxyphenyl side groups being reacted to form dihydroxyphenyl linkages.

2. The method of claim 1, said hydroxyphenyl side groups being reacted to form the dihydroxyphenyl linkages after said composition is provided in said space.

3. The method of claim 1, said hydroxyphenyl side groups being reacted to form the dihydroxyphenyl linkages contemporaneously or in conjunction with the provision of said composition in said space.

4. The method of claim 1, said collagen macromolecules comprising gelatin macromolecules.

5. The method of claim 1, said hydroxyphenyl side groups comprising tyramine side groups and the dihydroxyphenyl linkages comprising dityramine linkages.

6. The method of claim 5, wherein a ratio of said tyramine side groups to the sum of said tyramine side groups and all amino acids in said collagen macromolecules is about or less than 5%.

7. The method of claim 1, further comprising injecting the composition into the person or animal.

8. The method of claim 7, said composition being injected in the form of a first precursor and a second precursor that are injected using a first needle and a second needle, respectively, the second needle being partially located inside the first needle.

9. The method of claim 1, said hydroxyphenyl side groups being reacted with a peroxide in the presence of a peroxidase to form said dihydroxyphenyl linkages.

10. The method of claim 9, said composition comprising a first precursor that comprises the peroxidase or the peroxide but not both, and a second precursor that comprises the other of the peroxidase and peroxide that is not included in the first precursor.

11. The method of claim 1, wherein the pubo-urethral ligament is scarred as a result of providing said composition in said space.

12. The method of claim 1, the urinary incontinence being stress urinary incontinence.

13. The method of claim 1, said composition being provided via injection into said space between the urethra and the pubis of the person or animal, said side groups comprising tyramine groups, said dihydroxyphenyl linkages comprising dityramine linkages.

14. The method of claim 13, said tyramine side groups being reacted to form the dityramine linkages after said composition is injected in said space.

15. The method of claim 13, said tyramine side groups being reacted to form the dityramine linkages contemporaneously or in conjunction with the injection of said composition in said space.

16. The method of claim 13, said collagen macromolecules comprising gelatin macromolecules.

17. The method of claim 13, wherein a ratio of said tyramine side groups to the sum of said tyramine side groups and all amino acids in said collagen macromolecules is about or less than 5%.

18. The method of claim 13, said composition comprising a first precursor that comprises a peroxide or a peroxidase but not both, and a second precursor that comprises the other of the peroxide and peroxidase that is not included in the first precursor, said first and second precursors being injected using a first needle and a second needle, respectively, the second needle being partially located inside the first needle.

19. The method of claim 13, said tyramine side groups being reacted with a peroxide in the presence of a peroxidase to form said dityramine linkages.

20. The method of claim 13, wherein the pubo-urethral ligament is scarred as a result of injecting said composition in said space.

21. The method of claim 13, the urinary incontinence being stress urinary incontinence.

22. The method of claim 1, said composition being provided in said space via the steps of:
    injecting a first precursor into said space the first precursor comprising said macromolecules having said hydroxyphenyl side groups substituted thereon, and a peroxidase or a peroxide but not both, wherein a ratio of said hydroxyphenyl side groups to the sum of said hydroxyphenyl side groups and all amino acids in said macromolecules is about or less than 5%;
    injecting a second precursor into said space, said second precursor comprising the other of said peroxide and peroxidase not included in said first precursor; and
    reacting the hydroxyphenyl side groups on the macromolecules from said first precursor with peroxide in the presence of said peroxidase, at least one of the latter being from said second precursor, to form said dihydroxyphenyl linkages.

23. The method of claim 22, said first and second precursors being injected into said space contemporaneously.

24. The method of claim 23, said first and second precursors first coming into contact in conjunction with or immediately after their contemporaneous injection into said space.

25. The method of claim 24, the urinary incontinence being stress urinary incontinence.

26. The method of claim 1, said collagen macromolecules comprising gelatin.

27. The method of claim 22, said macromolecules comprising gelatin and said hydroxyphenyl side groups comprising tyramine groups, wherein said dihydroxyphenyl linkages comprise dityramine linkages.

28. A method of treating urinary incontinence comprising providing to a person or animal, in a space between a urethra and a pubis of the person or animal wherein the person's or animal's pubo-urethral ligament is disposed in the space, a composition comprising hydroxyphenyl-substituted macromolecules wherein at least a portion of said hydroxyphenyl side groups are reacted to form dihydroxyphenyl linkages, said macromolecules being selected from the group consisting of collagen, gelatin and hyaluronan.

29. The method of claim 28, said macromolecules comprising hyaluronan.

30. The method of claim 28, said hydroxyphenyl-substituted macromolecules comprising tyramine-substituted hyaluronan, said dihydroxyphenyl linkages comprising dityramine linkages.

31. The method of claim 28, said composition being provided to said person or animal by injecting the composition into said space.

32. The method of claim 31, said composition being injected as separately-injected first and second precursors, said first precursor comprising said hydroxyphenyl-substituted macromolecules and a peroxidase or a peroxide but not both, said second precursor comprising the other of said peroxide and peroxidase not included in said first precursor.

* * * * *